US007611693B2

(12) United States Patent
Yang et al.

(10) Patent No.: US 7,611,693 B2
(45) Date of Patent: Nov. 3, 2009

(54) MECHANISM-BASED TARGETED PANCREATIC BETA CELL IMAGING AND THERAPY

(75) Inventors: David J. Yang, Sugar Land, TX (US); Chang-Sok Oh, Houston, TX (US); Saady Kohanim, Sugar Land, TX (US); Dong-Fang Yu, Houston, TX (US); Ali Azhdarinia, Friendswood, TX (US); Jerry Bryant, Houston, TX (US)

(73) Assignee: Board of Regents, The Univerisity of Texas System, Austin, TX (US)

( * ) Notice: Subject to any disclaimer, the term of this patent is extended or adjusted under 35 U.S.C. 154(b) by 612 days.

(21) Appl. No.: 10/942,615

(22) Filed: Sep. 16, 2004

(65) Prior Publication Data

US 2005/0100506 A1    May 12, 2005

Related U.S. Application Data

(60) Provisional application No. 60/503,683, filed on Sep. 17, 2003.

(51) Int. Cl.
*A61K 49/00* (2006.01)
(52) U.S. Cl. ............ 424/9.1; 424/1.11; 424/1.65; 424/1.81; 534/14
(58) Field of Classification Search ............ 424/1.11, 424/1.37, 1.65, 1.69, 1.73, 9.1, 9.2, 9.3, 9.4, 424/9.5, 9.6, 9.7, 9.8, 1.49, 1.81; 534/7, 534/10–16
See application file for complete search history.

(56) References Cited

U.S. PATENT DOCUMENTS

| 4,379,785 | A | 4/1983 | Weyer et al. |
|---|---|---|---|
| 4,816,484 | A | 3/1989 | Toyoshima et al. |
| 4,915,931 | A | 4/1990 | Yokoyama et al. |
| 4,994,258 | A | 2/1991 | Burns et al. |
| 5,094,837 | A | 3/1992 | Bis |
| 5,416,105 | A | 5/1995 | Satoh et al. |
| 5,436,169 | A | 7/1995 | Iovanna et al. |
| 5,463,116 | A | 10/1995 | Sumikawa et al. |
| 6,312,661 | B1 | 11/2001 | Reubi |
| 6,774,109 | B2 * | 8/2004 | Dunmore et al. ............ 514/16 |
| 2002/0150896 | A1 | 10/2002 | Polonsky et al. |
| 2002/0155064 | A1 | 10/2002 | Reubi |
| 2002/0173636 | A1 | 11/2002 | Chen |
| 2003/0032021 | A1 | 2/2003 | Curtis |

FOREIGN PATENT DOCUMENTS

| JP | 57-102820 | 6/1982 |
|---|---|---|
| JP | 59-044329 | 3/1984 |
| JP | 59-193833 | 11/1984 |
| JP | 01-294700 | 11/1989 |
| JP | 05-186372 | 7/1993 |
| WO | WO 95/11006 | 4/1995 |
| WO | WO 01/44177 | 6/2001 |

OTHER PUBLICATIONS

Moore et al, Diabetes, Oct. 2001, vol. 50, pp. 2231-2236.*
Chachin, M., et al., "Nateglinide, A D-Phenylalanine Derivative Lacking Either a Sulfonylurea or Benzamido Moiety, Specifically Inhibits Pancreatic Beta-Cell-Type K(ATP) Channels," J. Pharmacol. Exp. Ther. 304(3):1025-32 (2003).
Chatziioannou, A., et al., "Imaging and Localization of Pancreatic Insulinomas," Journal of Clinical Imaging 25:275-283 (2001).
Chen, An-Shu, et al., "Antioxidant Activity of a Schiff Base of Pyridoxal and Aminoguanidine," Free Radical Biology & Medicine, 35(11):1392-1403 (2003).
Del Frate, C., et al., "Advances in Imaging for Pancreatic Disease," Curr Gastroenterol Rep. 4(2):140-8 (2002).
Hansen, A. M., et al., "Differential Interactions of Nateglinide and Repaglinide on the Human Beta-Cell Sulphonylurea Receptor 1," Diabetes 51(9):2789-95 (2002).
Hu, S. and Wang, S., "Effect of Insulinotropic Agent Nateglinide on Kv and Ca(2+) Channels in Pancreatic Beta-Cell," Eur. J. Pharmacol. 427(2):97-104 (2001).
Hu, S., et al., "Pancreatic Beta-Cell K(ATP) Channel Activity and Membrane-Binding Studies with Nateglinide: A Comparison with Sulfonylureas and Repaglinide," J. Pharmacol. Exp. Ther. 293(2):444-52 (2000).
Kalra, Mannudeep K., et al., "Current Status of Imaging in Pancreatic Diseases," Journal of Computer Assisted Tomography 26(5):661-675 (2002).
Malaisse, W. J., "On the Track to the Beta-Cell," Diabetologia 44(4):393-406 (2001).
Meyer, M., "Structural Requirements of Sulphonylureas and Analogues for Interaction with Sulphonylurea Receptor Subtypes," Br. J. Pharmacol. 128(1):27-34 (1999).
Moore, A., Bonner-Weir, S., and Weissleder, R., "Noninvasive In Vivo Measurement of Beta-Cell Mass in Mouse Model of Diabetes," Diabetes 50(10):2231-6 (2001).
Muller, G., "The Molecular Mechanism of the Insulin-Mimetic/Sensitizing Activity of the Antidiabetic Sulfonylurea Drug Amaryl," Mol. Med. 6(11):907-33 (2000).

(Continued)

*Primary Examiner*—D L Jones
(74) *Attorney, Agent, or Firm*—Vinson & Elkins LLP

(57) ABSTRACT

Compositions for imaging pancreatic beta cells comprise chelator-antidiabetic agent conjugates and optionally chelated metals.

10 Claims, 48 Drawing Sheets

OTHER PUBLICATIONS

Ohnota, H., "Novel Rapid- and Short-Acting Hypoglycemic Agent, A Calcium(2s)-2-Benzyl-3-(CisHexahydro-2-lsoindolinylcarbonyl) Propionate (KAD-1229) That Acts on the Sulfonylurea Receptor: Comparison of Effects Between KAD-1229 and Gliclazide," J. Pharmacol. Exp. Ther. 269(2):489-95 (1994).

Panten, U., Schwanstecher, M., and Schwanstecher, C., "Sulfonylurea Receptors and Mechanism of Sulfonylurea Action," Exp. Clin. Endocrinol Diabetes 104(1):1-9 (1996).

International Search Report dated Jan. 13, 2005.

Harris, et al., "Design, Synthesis, and Evaluation of Radiolabeled Integrin $\alpha_v\beta_3$ Receptor Antagonists for Tumor Imaging and Radiotherapy," Cancer Biotherapy & Radiopharmaceuticals, vol. 18:4, pp. 627-641 (2003).

Wild, et al., "DOTA-NOC, A High-Affinity Ligand of Somatostatin Receptor Subtypes 2, 3 and 5 for Labelling with Various Radiometals," European Journal of Nuclear Medicine and Molecular Imaging, vol. 30:10, pp. 1338-1347 (2003).

Heindel, et al, "Syntheses and Tissue Distribution of $^{99M}$Tc-Sulfonylureas," Journal of Pharmaceutical Sciences, vol. 64, No. 4, pp. 687-689 (1975).

Rosiere, et al, "Intraoperative gamma probe detection of insulinoma in an elderly patient with pancreatic cystic lesions," Clinical Endocrinology GV, vol. 57, No. 4, pp. 547-549 (2002).

Supplemental European Search Report dated Jun. 4, 2009.

* cited by examiner

| Observed ppm(DMSO-d6) | | Calcd. ppm | |
|---|---|---|---|
| 8.85 (d, 1H, J=1.1Hz) | d | 9.07 (1H) | d |
| 8.42 (d, 1H, J=1.1Hz) | c | 8.70 (1H) | c |
| 7.64 (d, 2H, J=8.4Hz) | k | 7.88 (2H) | k |
| 7.29 (d, 2H, J=8.4Hz) | j | 7.40 (2H) | j |
| 3.42 (t, 2H, J=7.2Hz) | g | 3.29 (2H) | g |
| 3.11 (m, 1H) | n | 3.58 (1H) | n |
| 2.80 (t, 2H, J=7.2Hz) | h | 2.81 (2H) | h |
| 2.41 (s, 3H) | a | 2.35 (3H) | a |
| 1.38-1.49 (m, 4H) | o | 1.51 (4H) | o |
| 0.87-1.10 (m, 6H) | p,q | 1.29 (6H) | p,q |

| Observed | | Calcd. (monomer) | |
|---|---|---|---|
| ppm | | ppm | |
| 179.5 (4C) | 4y | 176 (4C) | 4y |
| 177.9 | r | 170.7 | r |
| 165.8 | f | 167.9 | f |
| 161.7 | m | 160 | m |
| 157.9 | b | 156.5 | b |
| 144.6 | i | 143.4 | i |
| 143.5 | d | 143.3 | d |
| 142.2 | c | 142.9 | c |
| 142 | e | 142 | e |
| 141.5 | l | 136.5 | l |
| 129.6 (2C) | 2j | 128.2 (2C) | 2j |
| 126.7 (2C) | 2k | 125.4 (2C) | 2k |
| 59.1 (2C) | 2x | 59.1 | v |
| 58.6 (2C)?? | 2u, 2w | 58.8 (2C) | 2x |
| 56.4 | v | 58.4 | t |
| 52.9 | t | 52.7 | s |
| 51.4 | s | 52.4 (2C) | 2w |
| 49.4 | n | 52.0 (2C) | 2u |
| 40.7 | g | 46.9 | n |
| 39.2 (4C)?? | 2o | 44.9 | g |
| 34.9 | h | 37.2 | h |
| 33.1 | q | 32.7 (2C) | 2o |
| 25.5 | p | 27.1 | q |
| 24.8 | p | 21.6 (2C) | 2p |
| 21 | a | 20.9 | a |

| Observed ppm(DMSO-d6) | | Calcd. ppm | |
|---|---|---|---|
| 10.29 (s, 1H) | NH | | |
| 8.25 (t, 1H, J=5.6Hz) | NH | | |
| 7.84 (d, 2H, J=8.4Hz) | m | 7.88 (2H) | m |
| 7.64 (d, 1H, J=2.8Hz) | f | 7.85 (1H) | f |
| 7.50 (dxd, 1H, J=8.8, 2.8Hz) | c | 7.41 (1H) | d |
| 7.49 (d, 2H, J=8.4Hz) | l | 7.40 (2H) | l |
| 7.15 (d, 1H, J=8.8Hz) | d | 6.89 (1H) | c |
| 6.32 (d, 1H, J=7.8Hz) | NH | | |
| 3.80 (s, 3H) | a | 3.73 (3H) | a |
| 3.55 (q, 2H, J=6.8Hz) | i | 3.58 (1H) | p |
| 3.20-3.30 (m, 1H) | p | 3.53 (2H) | i |
| 2.94 (t, 2H J=6.9Hz) | j | 2.85 (2H) | j |
| 1.53-1.66 (m, 4H) | q | 1.51 (4H) | q |
| 1.46-1.50 (m, 1H) | r,s | 1.29 (6H) | r,s |
| 1.04-1.27 (m, 5H) | r,s | | |

| Observed ppm | | Calcd. ppm | |
|---|---|---|---|
| 163.7 | h | 167 | h |
| 155.8 | o | 162 | o |
| 150.6 | b | 158.9 | b |
| 145.3 | k | 143.4 | k |
| 138.3 | n | 136.5 | n |
| 131.6 | d | 133.3 | d |
| 129.7 | f | 128.7 | f |
| 129.4 (2C) | l | 128.2 (2C) | l |
| 127.4 (2C) | m | 126.2 | e |
| 124.8 | e | 125.4 (2C) | m |
| 124.5 | g | 120.5 | g |
| 114.2 | c | 115.6 | c |
| 56.3 | a | 55 | a |
| 48.2 | p | 46.9 | p |
| 40.3 | i | 45.7 | i |
| 34.8 | j | 37.2 | j |
| 32.4 (2C) | q | 32.7 (2C) | q |
| 25.1 | s | 27.1 | s |
| 24.3 (2C) | r | 21.6 (2C) | r |

| ppm | | ppm | |
|---|---|---|---|
| 7.62 (d, 2H, J=8.4Hz) | m | 7.88 (2H) | m |
| 7.45 (d, 1H, J=2.7Hz) | f | 7.85 (1H) | f |
| 7.33 (dxd, 1H, J=9.0Hz, J'=2.7Hz) | d | 7.41 (1H) | d |
| 7.28 (d, 2H, J=8.4Hz) | l | 7.40 (2H) | l |
| 6.91 (d, 1H, J=9.0Hz) | c | 6.89 (1H) | c |
| 3.94 (q, 1H, J=6.9Hz) | i | | a |
| 3.60 (s, 3H) | a | 3.73 (3H) | p |
| 3.55 (m, 1H) | p | 3.58 (1H) | i |
| 3.37 (s, 2H) | z | 3.53 (2H) | |
| 3.26 (s, 4H) | b' | | |
| 3.17 (s, 2H) | x | 3.30 (8H) | x,z,b' |
| 3.08 (s, 2H) | u | 3.25 (2H) | u |
| 2.95-3.01 (m, 4H) | v | 2.46 (8H) | v, w |
| 2.80-2.90 (m, 4h) | w | | |
| 2.74-2.84 (m, 2H) | j | 2.95 (2H) | j |
| 1.30-1.60 (m, 4H) | q | 1.51 (4H) | q |
| 0.85-1.10 (m, 6H) | r, s | 1.29 (6H) | r, s |

| Observed ppm(DMSO-d6) | | Calcd. ppm | |
|---|---|---|---|
| 10.49 (s, 1H) | NH | | |
| 8.55 (t, 1H, J=5.8Hz) | NH | | |
| 8.00 (d, 2H, J=8.4Hz) | m | 7.88 (2H) | m |
| 7.64 (d, 2H, J=8.4Hz) | l | 7.40 (2H) | l |
| 6.45 (d, 1H, J=7.7Hz) | NH | | |
| 4.35 (s, 3H) | f | 3.83 (2H) | f |
| 3.69 (q, 2H, J=6.8Hz) | i | 3.58 (1H) | p |
| 3.31-3.45 (m, 1H) | p | 3.49 (2H) | i |
| 3.09 (t, 2H< J=6.8Hz) | j | 2.81 (2H) | j |
| 2.37 (q, 2H, J=7.5Hz) | d | 2.00 (2H) | d |
| 2.20 (s, 3H) | a | 1.71 (3H) | a |
| 1.76-1.89 (m, 4H) | q | 1.65 (1H) | s |
| 1.39-1.47 (m, 1H) | s | 1.51 (4H) | q |
| 1.21-1.34 (m, 2H) | r | 1.25 (4H) | r |
| 1.16 (t, 3H, J=7.5Hz) | e | 1.06 (3H) | e |
| 1.04-1.12 (m, 2H) | r | 1.06 (3H) | t |
| 1.01 (d, 3H, J=6.5Hz) | t | | |

| Observed ppm | | Calcd. ppm | |
|---|---|---|---|
| 172.7 | g | 163.4 | g |
| 152.8 | o | 162 | h, o |
| 152.5 | h | | |
| 151.4 | k | 143.4 | k |
| 145.8 | b | 141.3 | b |
| 139.1 | n | 136.5 | n |
| 132.8 | c | 129 | c |
| 130 (2C) | l | 128.2 (2C) | l |
| 128.2 (2C) | m | 125.4 (2C) | m |
| 52.7 | f | 48 | f |
| 49.4 | i | 47.3 | i |
| 40.9 | p | 47.2 | p |
| 36 | j | 36.7 | j |
| 34.2 (2C) | q | 30.2 (2C) | q |
| 33.1 (2C) | r | 28.8 | s |
| 32.1 | s | 28.5 (2C) | r |
| 22.9 | t | 19.8 | t |
| 16.9 | d | 19 | d |
| 13.7 | a | 17.7 | a |
| 13.5 | e | 11.1 | e |

| Observed ppm(D2O) | | Calcd. ppm | |
|---|---|---|---|
| 7.89 (d, 2H, J=8.0Hz) | m | 7.88 (2H) | m |
| 7.55 (d, 2H, J=8.4Hz) | l | 7.40 (2H) | l |
| 4.29 (s, 2H) | f | 3.83 (2H) | f |
| 4.23 (q, 2H, J=6.8Hz) | i | 3.58 (1H) | p |
| 3.85-3.95 (m, 1H) | p | 3.49 (2H) | i |
| 3.67 (s, 4H) | c' | 3.30 (8H) | y, a, c' |
| 3.58 (s, 2H) | y | | |
| 3.48 (s, 2H) | a' | | |
| 3.36 (m, 4H) | w | 3.25 (2H) | v |
| 3.29 (m, 4H) | x | 2.81 (2H) | j |
| 3.09 (t, 2H< J=6.8Hz) | j | 2.46 (8H) | w, x |
| 2.97 (s, 2H) | v | | |
| 2.37 (q, 2H, J=7.5Hz) | d | 2.00 (2H) | d |
| 2.00 (s, 3H) | a | 1.71 (3H) | a |
| 1.76-1.89 (m, 4H) | q | 1.65 (1H) | s |
| 1.39-1.47 (m, 1H) | s | 1.51 (4H) | q |
| 1.21-1.34 (m, 2H) | r | | |
| 1.16 (t, 3H, J=7.5Hz) | e | 1.25 (4H) | r |
| 1.04-1.12 (m, 2H) | r | 1.06 (3H) | e |
| 1.01 (d, 3H, J=6.5Hz) | t | 1.06 (3H) | t |

| Observed ppm(D2O) | | Calcd. ppm | |
|---|---|---|---|
| 7.89 (d, 2H, J=8.0Hz) | m | 7.88 (2H) | m |
| 7.55 (d, 2H, J=8.4Hz) | l | 7.40 (2H) | l |
| 4.29 (s, 2H) | f | 3.83 (2H) | f |
| 4.23 (q, 2H, J=6.8Hz) | i | 3.58 (1H) | p |
| 3.85-3.95 (m, 1H) | p | 3.49 (2H) | i |
| 3.67 (s, 4H) | c' | 3.30 (8H) | y, a, c' |
| 3.58 (s, 2H) | y | | |
| 3.48 (s, 2H) | a' | | |
| 3.36 (m, 4H) | w | 3.25 (2H) | v |
| 3.29 (m, 4H) | x | 2.81 (2H) | j |
| 3.09 (t, 2H< J=6.8Hz) | j | 2.46 (8H) | w, x |
| 2.97 (s, 2H) | v | | |
| 2.37 (q, 2H, J=7.5Hz) | d | 2.00 (2H) | d |
| 2.00 (s, 3H) | a | 1.71 (3H) | a |
| 1.76-1.89 (m, 4H) | q | 1.65 (1H) | s |
| 1.39-1.47 (m, 1H) | s | 1.51 (4H) | q |
| 1.21-1.34 (m, 2H) | r | | |
| 1.16 (t, 3H, J=7.5Hz) | e | 1.25 (4H) | r |
| 1.04-1.12 (m, 2H) | r | 1.06 (3H) | e |
| 1.01 (d, 3H, J=6.5Hz) | t | 1.06 (3H) | t |

# MECHANISM-BASED TARGETED PANCREATIC BETA CELL IMAGING AND THERAPY

CROSS-REFERENCE TO RELATED APPLICATIONS

This application claims benefit of priority of U.S. Ser. No. 60/503,683 filed Sep. 27, 2003.

BACKGROUND OF THE INVENTION

In the United States, approximately 16 million people (6 percent of the population) suffer from diabetes mellitus. Every year, about 800,000 new cases are diagnosed and another 6 million people remain unaware that they have the disease. Diabetes mellitus kills about 193,000 U.S. residents each year, and it is the seventh leading cause of all deaths and the sixth leading cause of all deaths caused by disease. There is a steady rise in children developing type 2 diabetes. In Canada, more than 2.2 million residents (7 percent of the population) have diabetes mellitus, and the disease contributes to more than 25,000 deaths a year.

Adenocarcinoma of the pancreas is the fifth most common cause of cancer death in the United States. In the U.S., almost 45,000 people become affected with pancreatic cancer every year. Cancer most often occurs in the pancreatic head and often leads to biliary obstruction with a clinical presentation of painless jaundice. The 5 year survival rate for resectable patients is about 10% with a median survival of 12 to 18 months. Unresectable patients live about 6 months. Both diseases are associated with pancreatic function. Also, risk for pancreatic cancer is increased in adult-onset diabetics.

In the pancreas, the Islets of Langerhans are composed of four cell types, each of which synthesizes and secrets a distinct polypeptide hormone: insulin in the beta cell (60%), glucagon in the alpha cell (25%), somatostatin in the D cell (10%), and pancreatic polypeptide in the F cell (5%). Beta cells are the major type of cells in the pancreas. Certain nutrients and growth factors can stimulate pancreatic beta-cell growth. However, the appropriate mitogenic signaling pathways in beta-cells have been relatively undefined. This failure to define these important signaling pathways is due at least in part to a lack of effective imaging technologies.

The current status of imaging in pancreatic diseases has been recently reviewed by Kalra et al. *Journal of Computer Assisted Tomography* 26:661-675. The reviewed technologies include CT, MRI, EUS and PET scans.

SUMMARY

The present disclosure addresses at least in part some deficiencies in the prior art by providing novel DTPA-antidiabetic conjugates useful for imaging beta-cell function. Through binding of radiolabeled conjugates, such as $^{99m}$Tc-DTPA-antidiabetic conjugates, for example, to pancreatic beta receptors, detectable by gamma scintigraphy, pancreatic function is monitored. Four DTPA-antidiabetic conjugates have been synthesized and evaluated. Animal studies have shown that DTPA-nateglinide and DTPA-glipizide are able to selectively image pancreatic beta cells with no acute toxicity at the given doses. These agents are labeled with isotopes in order to assess beta cell function in diabetic or insulinoma patients both pre- and post-treatment. These compositions and methods are useful to provide early diagnosis as well as monitoring of response of pancreatic disease during treatment.

The present invention may be described in certain embodiments therefore as a composition comprising an antidiabetic agent, a chelator and a chelated metal ion. It is further understood that the composition may be a prodrug comprising an antidiabetic agent conjugated to a chelator to which a metal may be added. In such an embodiment, various metals may be added to the composition as appropriate for different diagnostic or therapeutic applications or for different types of imaging as described herein. The use of compositions comprising metals or metal ions in the in vivo imaging of mammalian tissues or organs including human organs is well known in the art, and any of such uses of an appropriate metal for a particular type of detection is contemplated by the present disclosure.

The compositions of the present disclosure may include, therefore, metals appropriate for contrast enhanced imaging or for scintigraphic imaging PET, MRI, or even CT imaging. The metal may be a radionuclide, including beta or gamma emitters, or it may be a magnetic or paramagnetic metal ion as needed. Preferred metals and metal ions for use in the described compositions and methods include, but are not limited to ions and isotopes of iron, manganese, chromium, copper, nickel, gadolinium, erbium, europium, dysprosium, holmium, gallium, germanium, cobalt, calcium, rubidium, yttrium, technetium, ruthenium, rhenium, indium, iridium, platinum, thallium, samarium, or boron, and most preferred metal ions for imaging include technetium (Tc-99m), gallium (Ga-67, 68), copper (Cu-60-64), gadolinium (Gd), holmium (Ho-166), or holmium (Re-187, 188); preferred metal ions for therapeutics include isotopes of yttrium, rhenium, copper and holmium.

The chelators of the disclosed compositions may be any appropriate chelators known in the art, including, but not limited to diethylenetriamine pentaacetic acid (DTPA), ethylene diamine tetra-acetic acid (EDTA), cyclohexyl 1,2-diamine tetra-acetic acid (CDTA), dimercaptosuccinic acid (DMSA), triglycinbenzoyl thiol (MAG-3), methylenebisphophonate (MDP), ethyleneglycol-0,0'bis (2-aminoethyl)-N,N, N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetraacetic acid (DOTA), hydroxyethyldiamine triacetic acid (HEDTA), or 1,4,8,11-tetra-azacyclo-tetradecane-N,N',N'',N'''-tetra-acetic acid (TETA). In the most preferred embodiments the chelator is DTPA.

The antidiabetic agents of the disclosed inventions may be any antidiabetic drugs known in the art, or any compounds that bind to or associate preferentially with beta cells of the pancreas. The most preferred agents are those that bind to a surface receptor on beta cells, including various sulphonylurea receptors such as SUR-1, SUR2A and SUR2B as well as other receptors such as the GLP-1 receptor or the somatostatin receptor. Preferred antidiabetic agents include nateglinide, L-nateglinide, repaglinide, tolbutamide, glibenclamide, Amaryl, glipizide, glyburide, gliclazide, glimepiride, and most preferably nateglinide, glipizide, glyburide, or glimepiride.

In certain embodiments the compositions of the present inventions may include any of the mentioned compounds or elements in any combination, and preferably include $^{99m}$Tc-DTPA-nateglinide, $^{99m}$Tc-DTPA glipizide, $^{99m}$Tc-DTPA-glyburide or $^{99m}$Tc-DTPA-glimepiride for gamma imaging.

In certain embodiments, the present invention may be described as a method of treating a pancreatic disease comprising administering to a subject in need thereof a composition comprising an antidiabetic agent a chelator and a chelated metal ion, wherein the metal ion is a beta emitter. A subject in need thereof may include any animal or human subject that has, or is subject to developing a pancreatic disease including, but not limited to diabetes, pancreatitis, hyperinsulinemia or insulinoma. Subjects may be identified by various methods known in the clinical arts, including monitoring glucose tolerance, insulin resistance, blood insulin levels, blood glucose levels, major histocompatibility complex typing, certain antibodies, weight gain or loss, obesity, or even family history and genetic profiles.

Compositions as described herein are useful in a number of applications, both diagnostic, prognostic and therapeutic. As such, certain embodiments of the invention may be described as methods of imaging a mammalian pancreas comprising administering to the mammal a composition comprising an antidiabetic agent, a chelator and a chelated metal ion and detecting an image of the pancreas. As described, the image may be a gamma image, a PET image, an MRI image, or other types of images known in the art.

Exemplary methods include methods of monitoring pancreatic beta cell mass or morphology in a mammal, useful for monitoring the condition of the pancreas in a susceptible subject prior to onset of a pancreatic disease, or monitoring progress of a disease, or even methods of monitoring the outcome of certain therapies during treatment or management of a pancreatic disease. The methods of the inventions may be used therefore to monitor beta cell mass, cell number, function, or lymphocyte infiltration into the beta cell mass.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
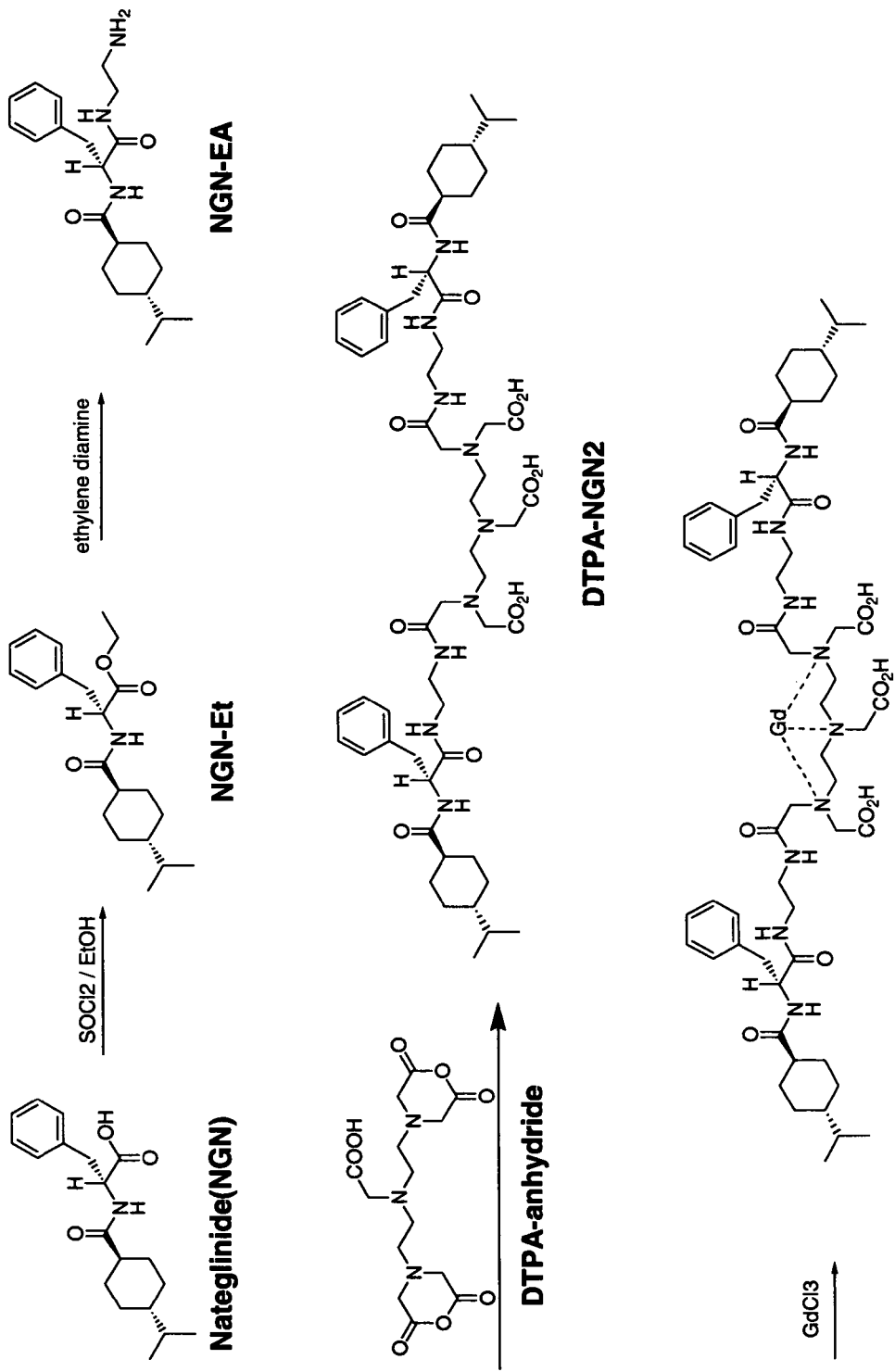
FIG. 1 is a synthetic scheme of metal-($^{99m}$Tc, Gd) DTPA-NGN2.

The present disclosure provides compositions and methods to improve the diagnosis and treatment of pancreatic associated diseases including, but not limited to diabetes, pancreatitis, insulinoma, adenocarcinoma, islet cell tumor, islet hypertrophy in diabetics and hyperinsulinemia based on the discovery of compositions and methods for the imaging of beta cells in vivo as well as the delivery of agents of therapeutic value specifically to pancreatic beta cells.

This disclosure is based on the development of compositions and methods for mechanism-based targeting of beta-cells for imaging and therapeutic purposes. In preferred embodiments, the disclosed compositions include an antidiabetic agent, a chelator, and optionally a chelated metal ion. The present inventors have successfully demonstrated scintigraphic visualization of the pancreas in rat and rabbit animal models using such compositions, including $^{99m}$Tc-DTPA-nateglinide (NGN) and $^{99m}$Tc-DTPA-glipizide.

The antidiabetic agents of the present disclosure are preferably agents that preferentially interact with or bind to specific receptors on the pancreatic beta cells. Such agents may bind to the sulphonylurea receptors, including SUR1, SUR2A and SUR2B, GLP-1 receptor, somatostatin receptor, angiotensin II receptor, and/or bradykinin receptor. Preferred agents include, but are not limited to nateglinide, L-nateglinide, repaglinide, tolbutamide, glibenclamide, Amaryl, glipizide, glyburide, gliclazide, and glimepiride.

In certain preferred embodiments, the chelator of the disclosed compositions is diethylenetriamine pentaacetic acid (DTPA). Other chelators may also be used in the practice of the disclosure, including but not limited to ethylene diamine tetra-acetic acid (EDTA), cyclohexyl 1,2-diamine tetra-acetic acid (CDTA), ethyleneglycol-0,0'bis (2-aminoethyl)-N,N,N', N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetraacetic acid (DOTA), hydroxyethyldiamine triacetic acid (HEDTA), 1,4, 8,11-tetra-azacyclo-tetradecane-N,N',N'',N'''-tetra-acetic acid (TETA) dimercaptosuccinic acid (DMSA), triglycinbenzoyl thiol (MAG-3) and methylenebisphophonate (MDP). The preferred metal ions for imaging include technetium (Tc-99m), gallium (Ga-67, 68), copper (Cu-60-64), gadolinium (Gd), holmium (Ho-166), or holmium (Re-187, 188); preferred metal ions for therapeutics include yttrium, rhenium, copper and holmium.

Metal chelators useful in this disclosure include those which contain cationic, basic and basic-amine groups and which chelate metals and metal ions, transition elements and ions, and lanthanide series elements and ions. It will be apparent to those skilled in the art that essentially any single atomic element or ion amenable to chelation by a cationic, basic and amine-containing chelator, may also be useful in this disclosure.

Aqueous compositions of the present inventions comprise an effective amount of the described compositions dissolved and/or dispersed in a pharmaceutically acceptable carrier and/or aqueous medium. The phrases "pharmaceutically and/or pharmacologically acceptable" refer to molecular entities and/or compositions that do not produce an adverse, allergic and/or otherwise untoward reaction when administered to an animal, and/or a human, as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the compositions is contemplated. Supplementary active ingredients can also be incorporated into the compositions.

Aqueous carriers may include water, alcoholic/aqueous solutions, saline solutions, parenteral vehicles such as sodium chloride, Ringer's dextrose, etc. Intravenous vehicles may include fluid and nutrient replenishers. Preservatives may include antimicrobial agents, anti-oxidants, chelating agents and inert gases. The pH and exact concentration of the various components in the pharmaceutical are adjusted according to well known parameters.

For purposes of this disclosure, preferred metal ions are generally those known in the art to be useful for imaging techniques including, but not limited to gamma scintigraphy, magnetic resonance, positron emission tomography, and computed tomography. Metal ions useful for chelation in paramagnetic T1-Type MRI contrast agent compositions and uses may include divalent and trivalent cations orf metals selected from iron, manganese, chromium, copper, nickel, gadolinium, erbium, europium, dysprosium and holmium. Chelated metal ions generally useful for radionuclide imaging and in radiotherapeutic compositions and uses, may include metals selected from gallium, germanium, cobalt, calcium, rubidium, yttrium, technetium, ruthenium, rhenium, indium, iridium, platinum, thallium and samarium. Metal ions useful in neutron-capture radiation therapy may include boron and others with large nuclear cross sections. Metal ions useful in Ultrasound contrast and X-Ray contrast compositions and uses may, provided they achieve adequate site concentrations, include any of the metal ions listed above, and in particular, may include metal ions of atomic number at least equal to that of iron.

The compositions may be provided "cold" (without a radioisotope label) or they may be provided with a label. Various radioactive labels may be used, as suited to a particular application. For example, a $^{99m}$Tc label may be preferred for gamma imaging, $^{61}$Cu— for PET imaging, gadolinium for MRI and $^{188}$Re ($^{166}$Ho—) for internal radiotherapeutic applications.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of DTPA-Nateglinide (DTPA-NGN)

DTPA-nateglinide was synthesized in a two-step manner. The synthetic scheme is shown in FIG. 1.

Step 1. Synthesis of Aminoethyl Amide Analogue of Nateglinide

Figure 2:
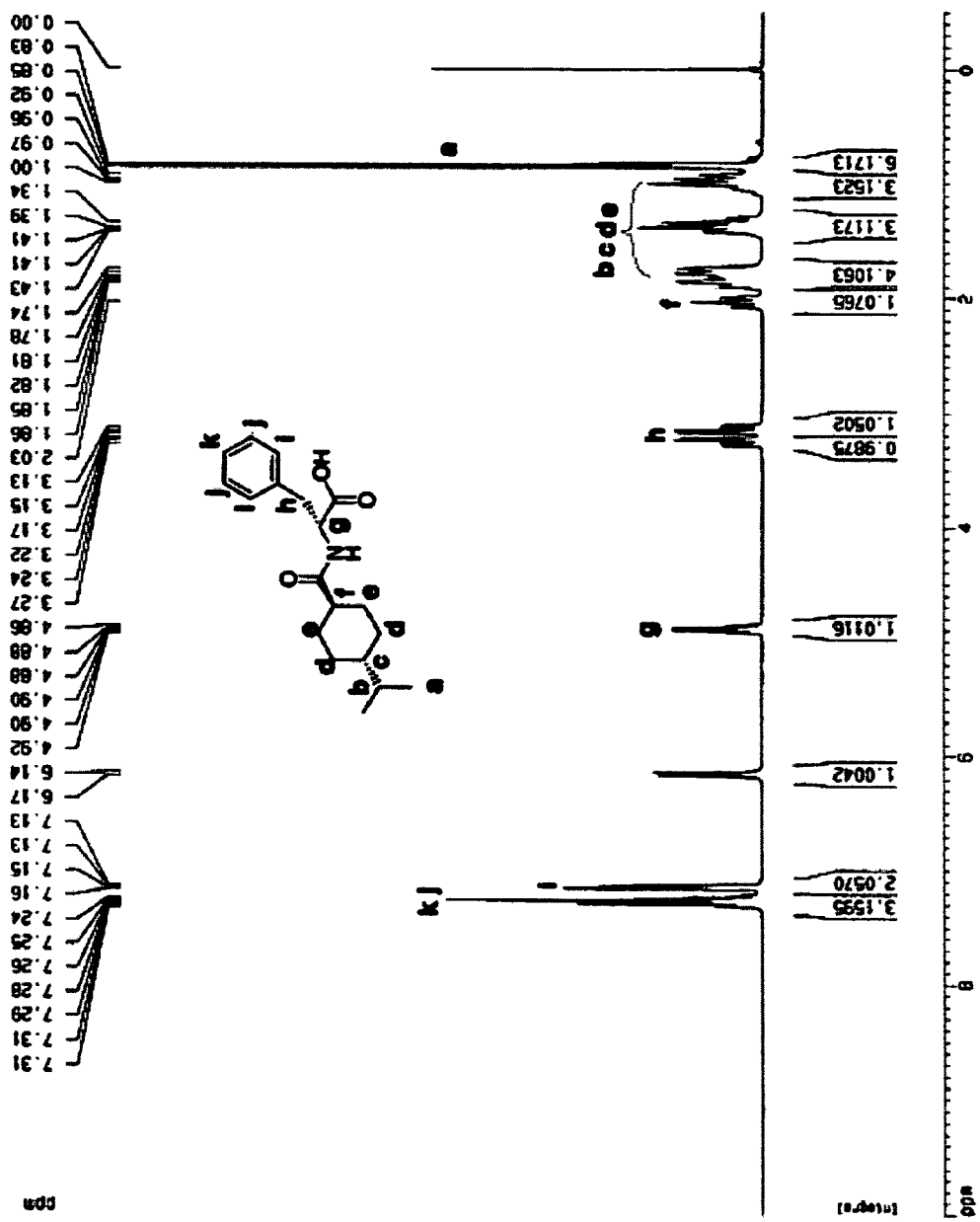
FIG. 2 is $^1$H-NMR spectrum of Nateglinide.
Figure 3:
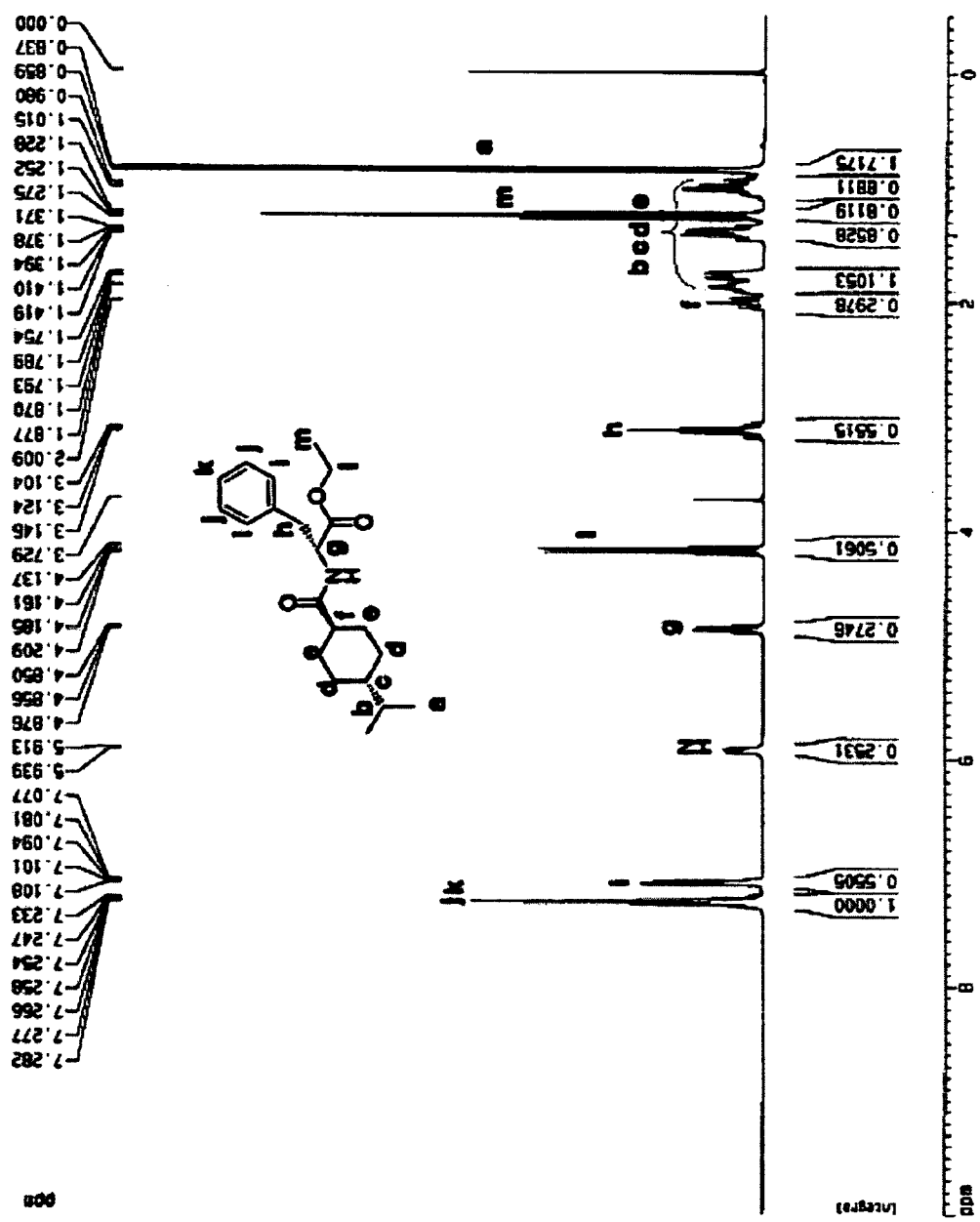
FIG. 3 is $^1$H-NMR spectrum of NGN-Et.

Nateglinide (3.1742 g, 10 mmol) was dissolved in 20 mL of ethyl alcohol. Thionyl Chloride (5.1 mL, 70 mmol) was added dropwise to the solution. The reaction mixture was stirred overnight and the solvent was evaporated at reduced pressure. FIGS. 2 and 3 showed $^1$H-NMR of nateglinide and its ester form.

Figure 4:
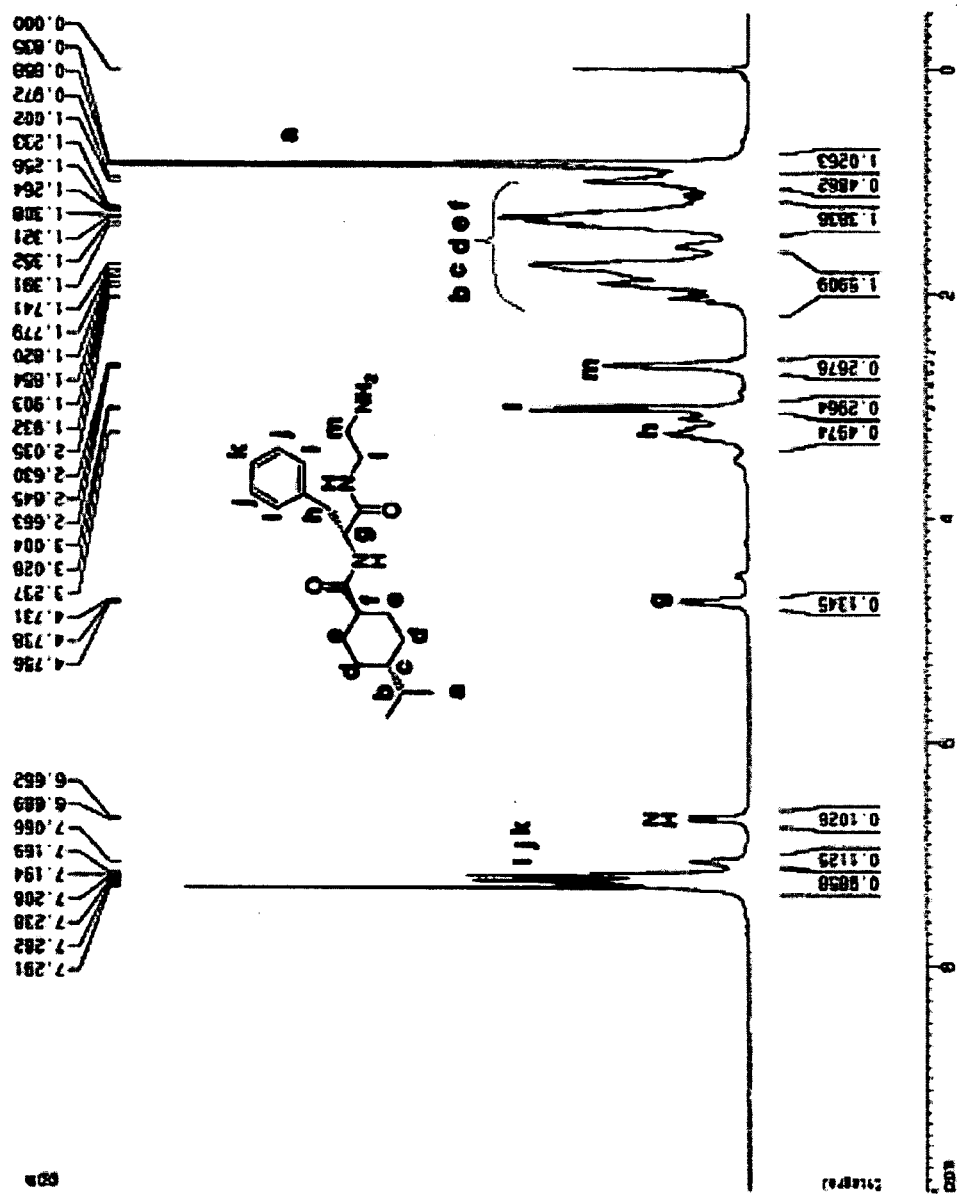
FIG. 4 is $^1$H-NMR spectrum of NGN-EA.
Figure 5:
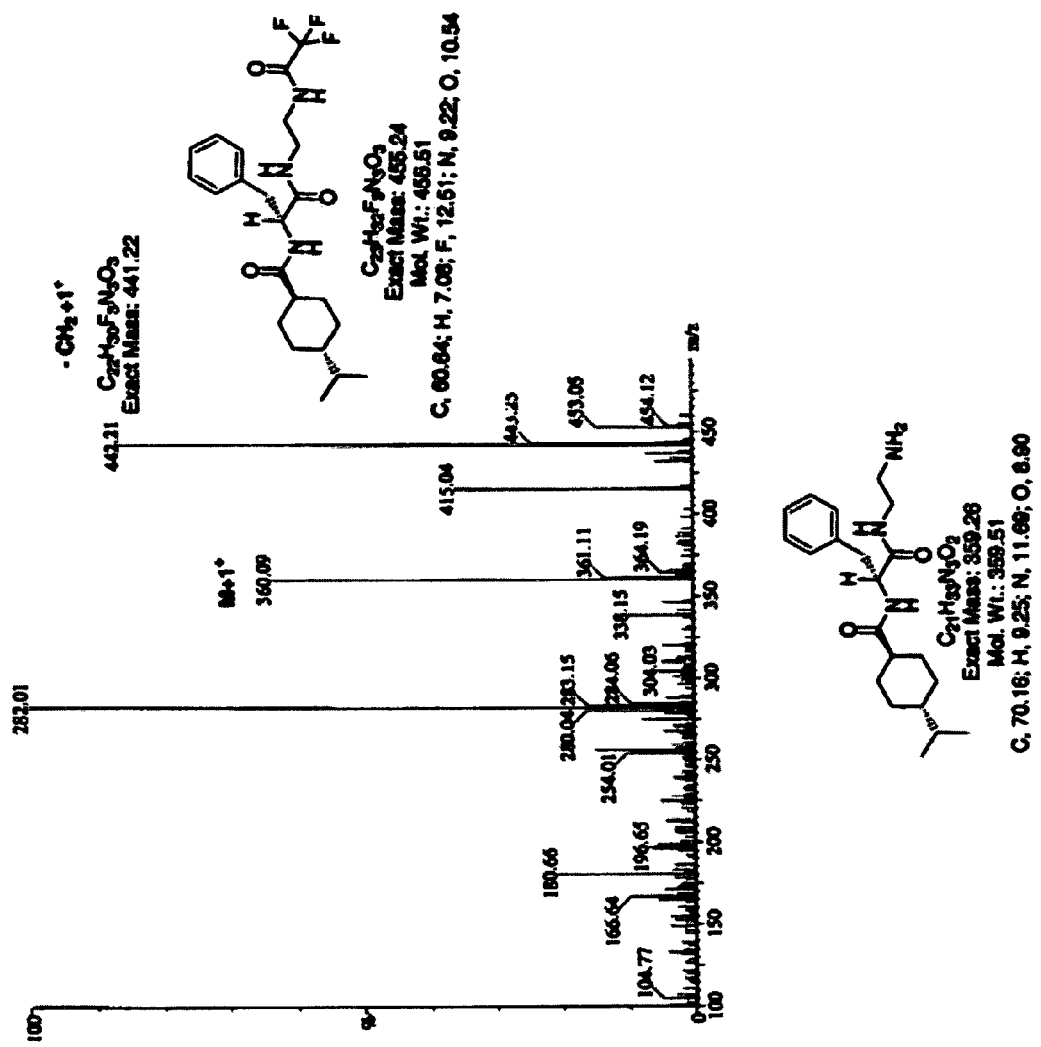
FIG. 5 is the Mass Spectrum of NGN-EA.

Ethyl alcohol (20 mL) and ethylene diamine (3.4 mL, 50 mmol) were added. The mixture was stirred overnight. The solvent was evaporated at reduced pressure. The solid was dissolved in chloroform (50 mL) and washed with water (2×50 mL). The chloroform layer was dried over anhydrous magnesium sulfate. The solvent was filtered and evaporated at reduced pressure. Aminoethyl amide analogue of nateglinide was obtained as a white solid (3.559 g, 99% yield). FIGS. 4 and 5 showed $^1$HNMR and mass spectrometry of aminoethyl amide analogue of nateglinide.

Step 2. Synthesis of DTPA-Nateglinide

Figure 6:
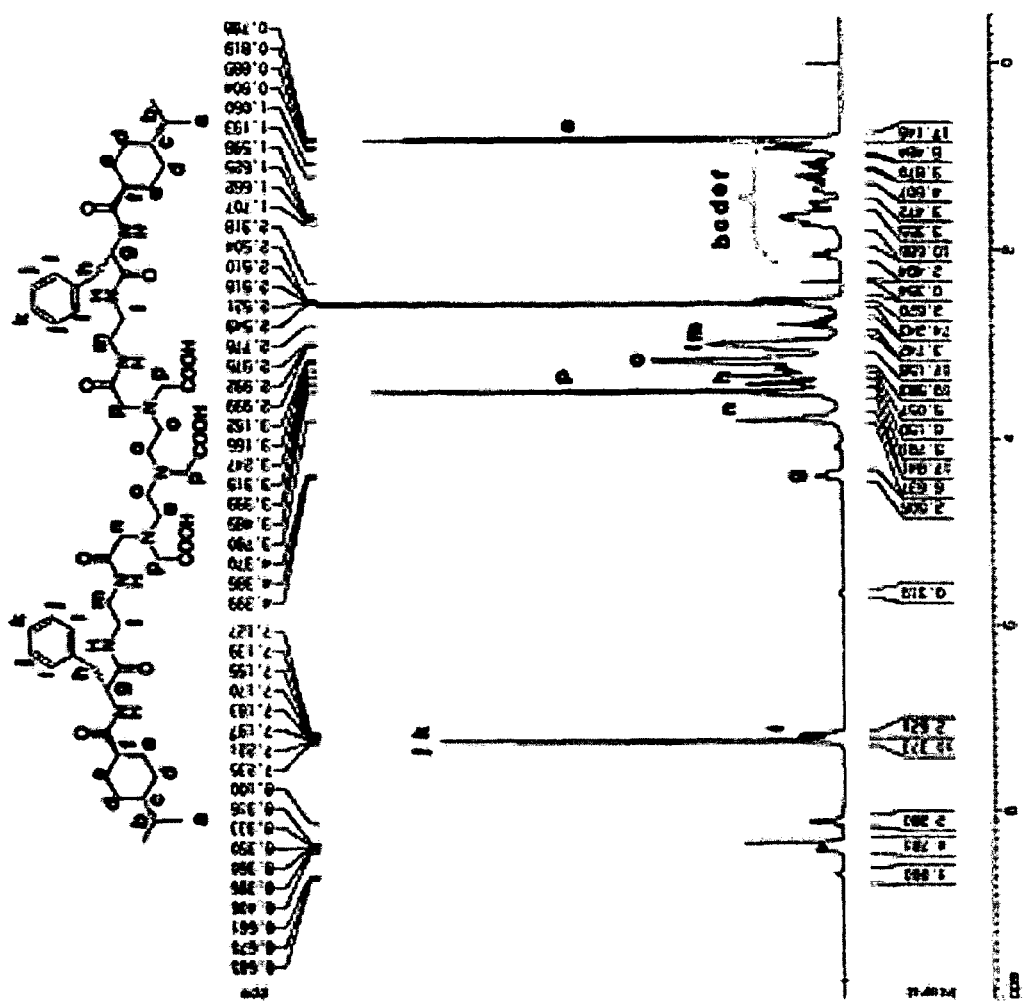
FIG. 6 is $^1$H-NMR spectrum of NGN2.
Figure 7:
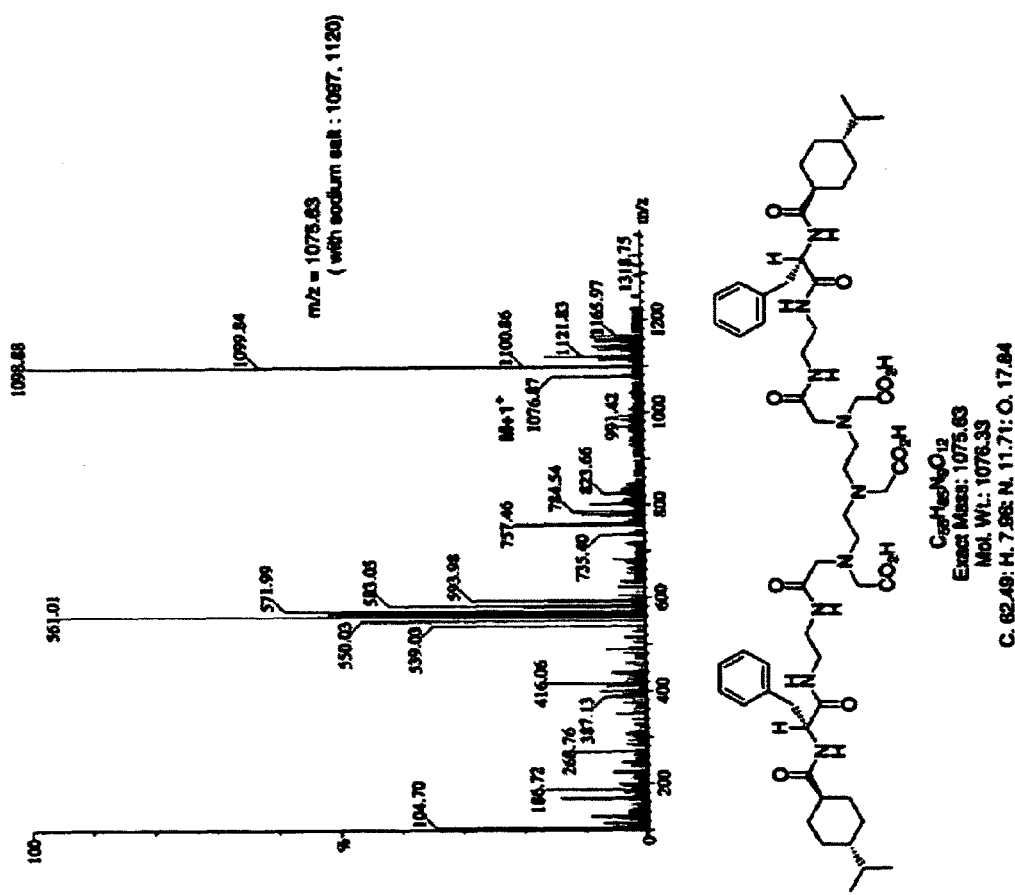
FIG. 7 is the Mass Spectrum of DTPA-NGN2.

Aminoethyl amide analogue of nateglinide (359.5 mg, 1.0 mmol) was dissolved in DMSO (anhydrous, 10 ml). DTPA-dianhydride (178.7 mg, 0.5 mmol) and triethyl amine (279 uL, 2.0 mmol) were added to the solution and the mixture was heated at 60° C. for 4 hours. After cooling, water (8 mL) and 1N-sodium bicarbonate solution (8 mL) were added. The mixture was stirred for 2 hours. The aqueous phase was dialyzed with membrane (MW CO<500) for 2 days. DTPA-NGN (413.9 mg, 87.7% yield) as a white solid was gathered after lyophilization. FIGS. 6 and 7 showed $^1$H-NMR and mass spectrometry of DTPA-Nateglinide.

Example 2

Synthesis of DTPA-Glipizide (DTPA-GLP)

Figure 8:
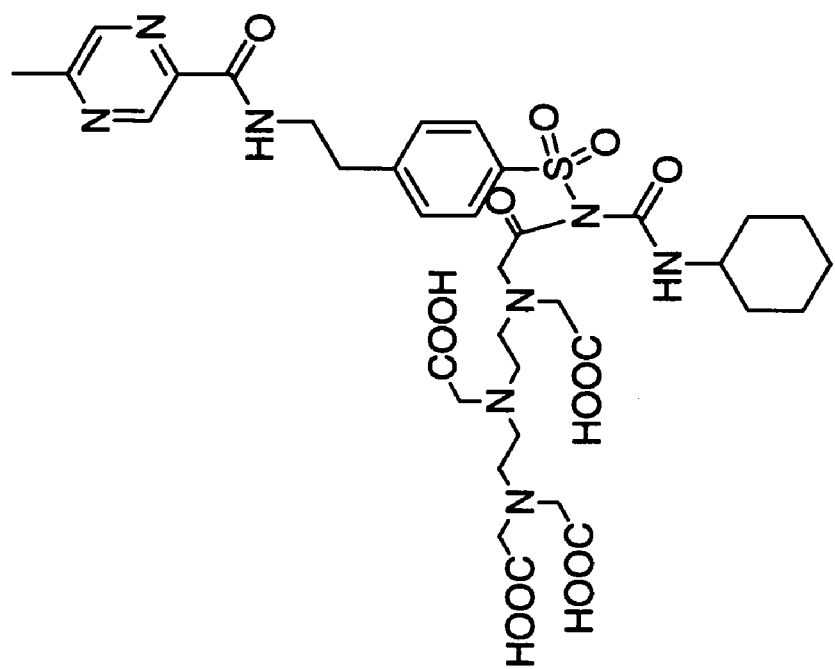
FIG. 8 is a synthetic scheme of DTPA-GLP.
Figure 8:
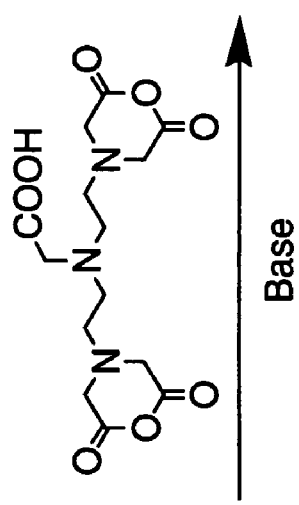
Figure 8:
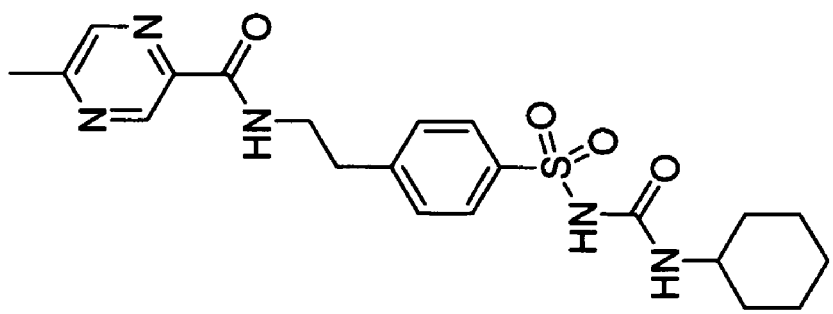
Figure 9:
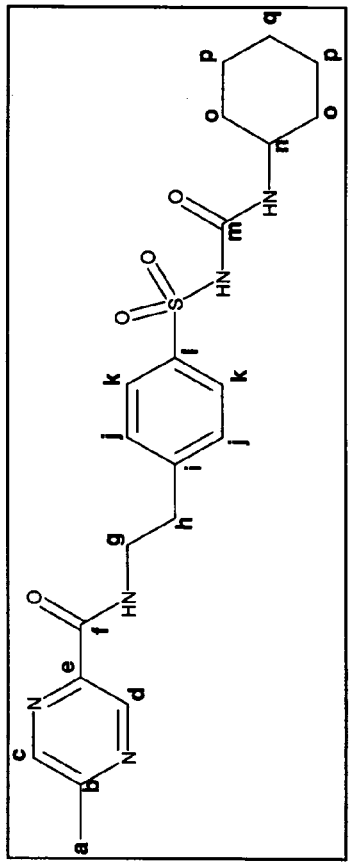
FIG. 9 is $^1$H-NMR data of Glipizide.
Figure 10:
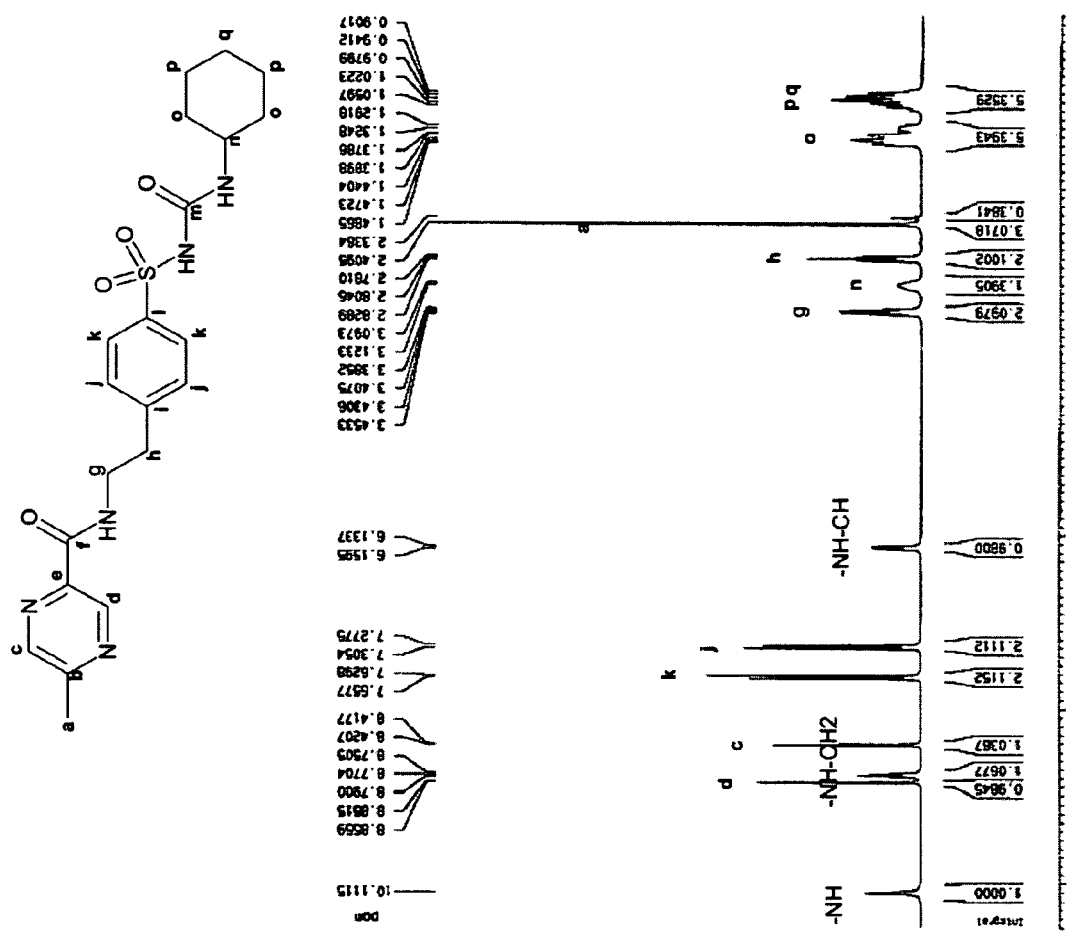
FIG. 10 is $^1$H-NMR spectrum of Glipizide.
Figure 11:
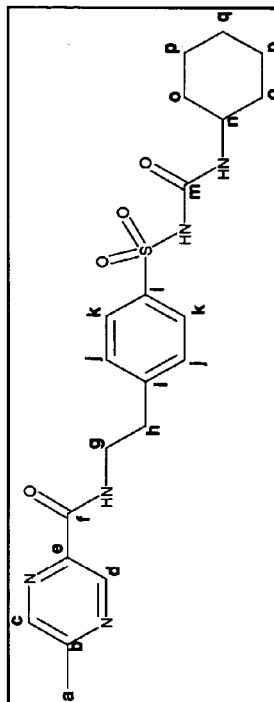
FIG. 11 is $^{13}$C-NMR data of Glipizide.
Figure 12:
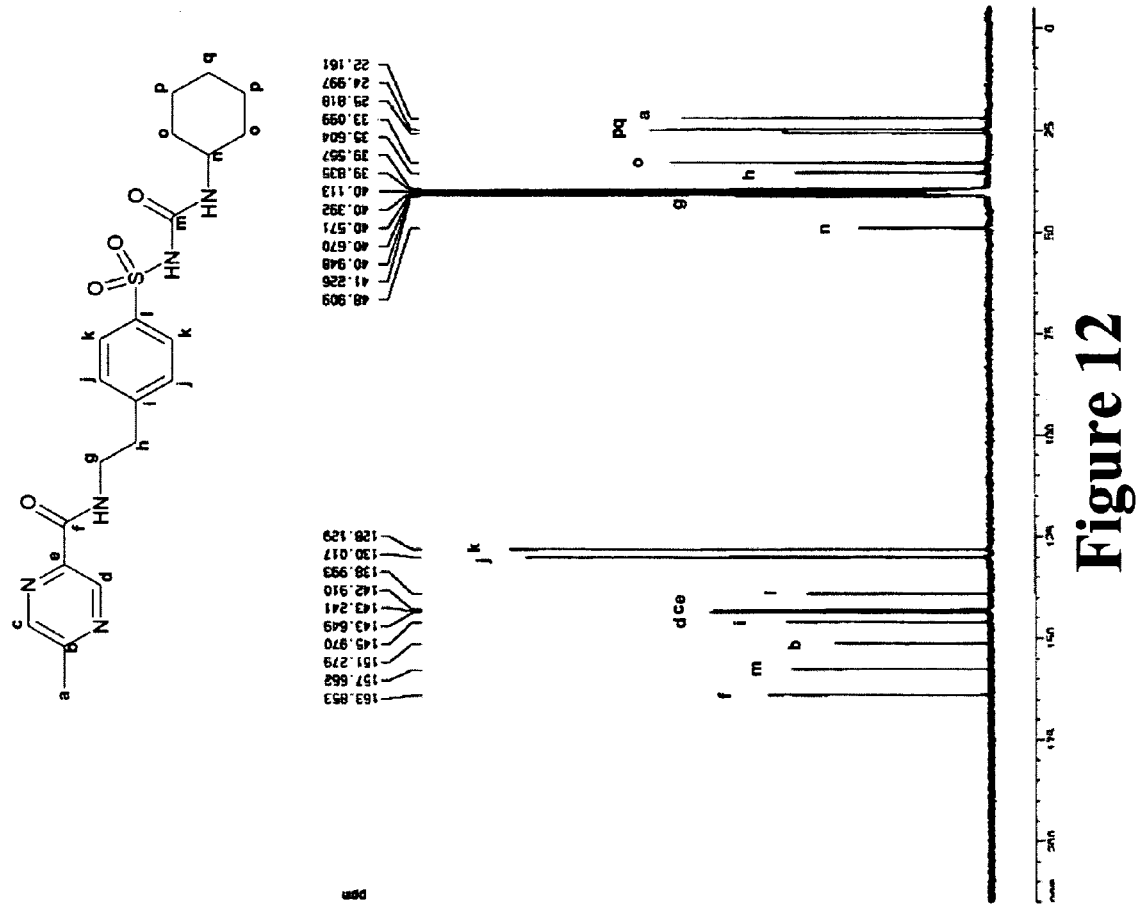
FIG. 12 is the $^{13}$C-NMR spectrum of Glipizide.
Figure 13:
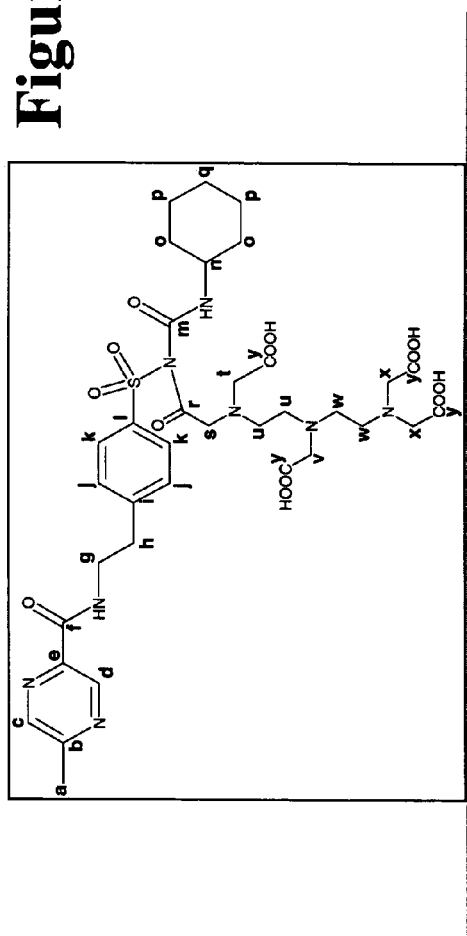
FIG. 13 is $^1$H-NMR data of DTPA-Glipizide.
Figure 14:
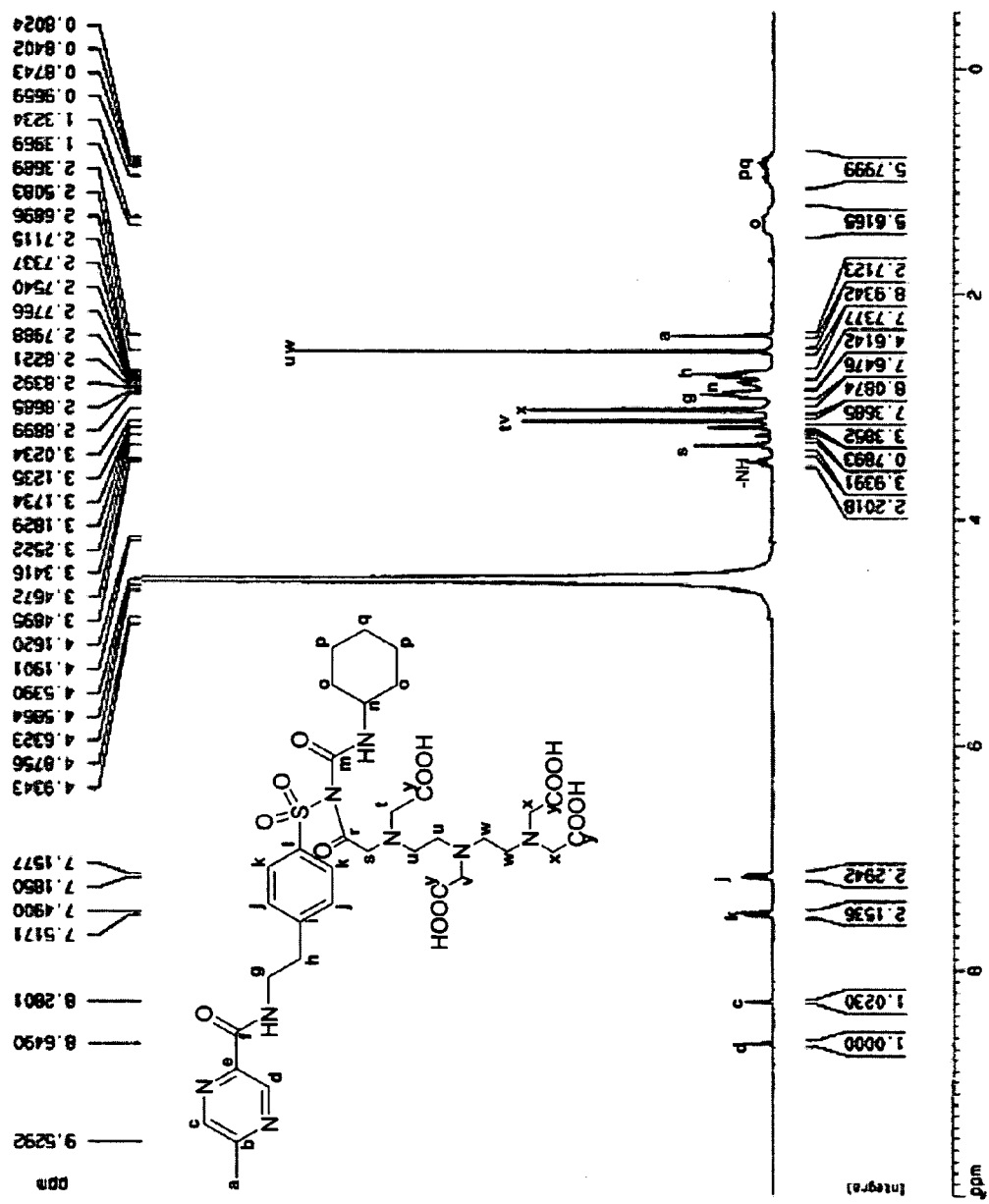
FIG. 14 is $^1$H-NMR spectrum of DTPA-Glipizide.
Figure 15:
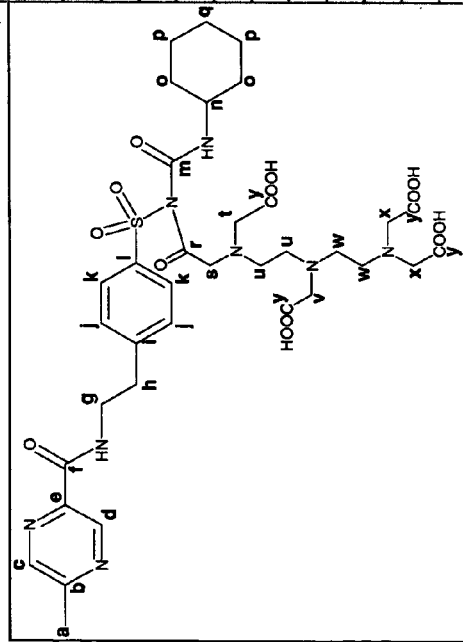
FIG. 15 is $^{13}$C-NMR data of DTPA-Glipizide.
Figure 16:
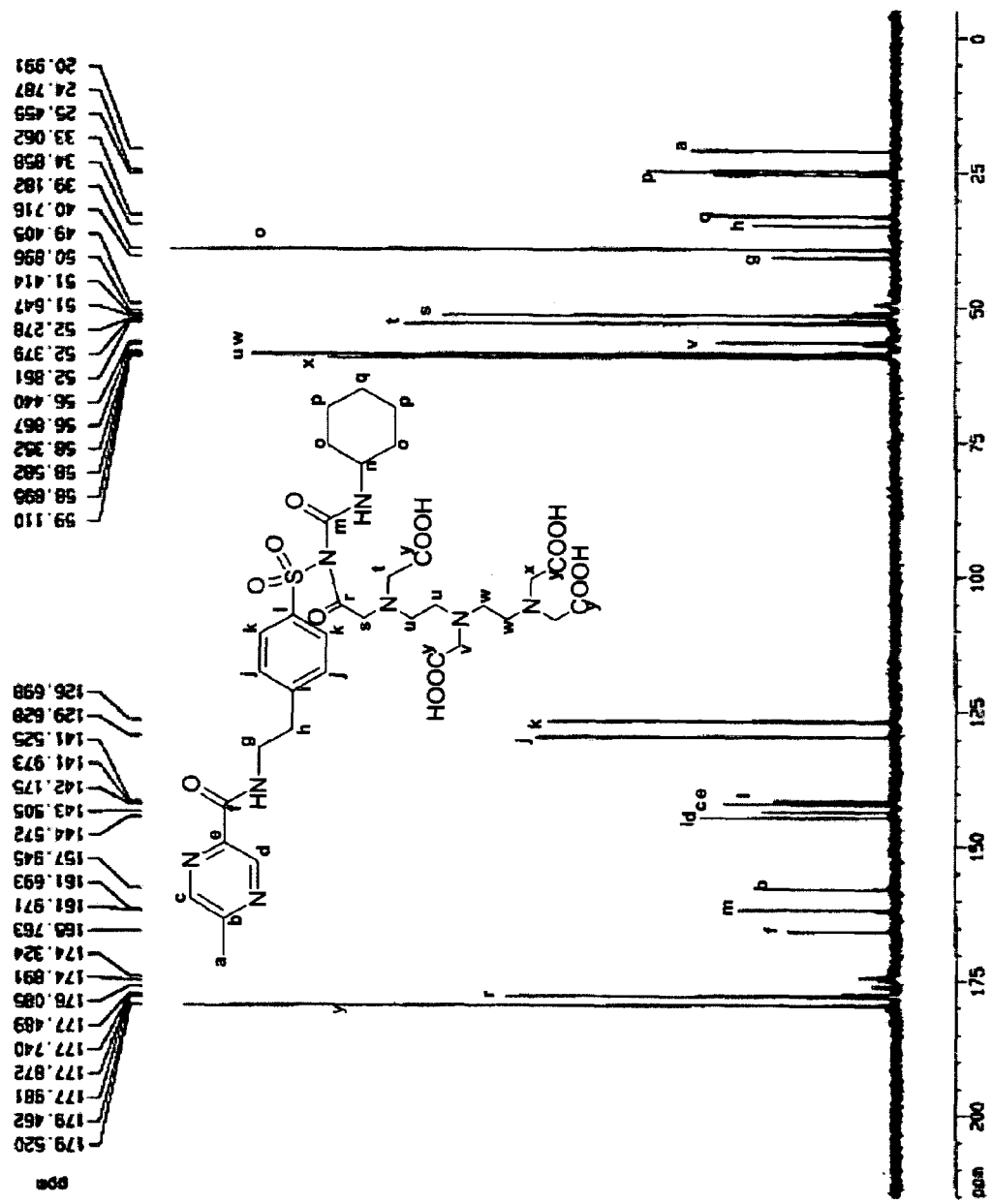
FIG. 16 is $^{13}$C-NMR spectrum of DTPA-Glipizide.
Figure 17:
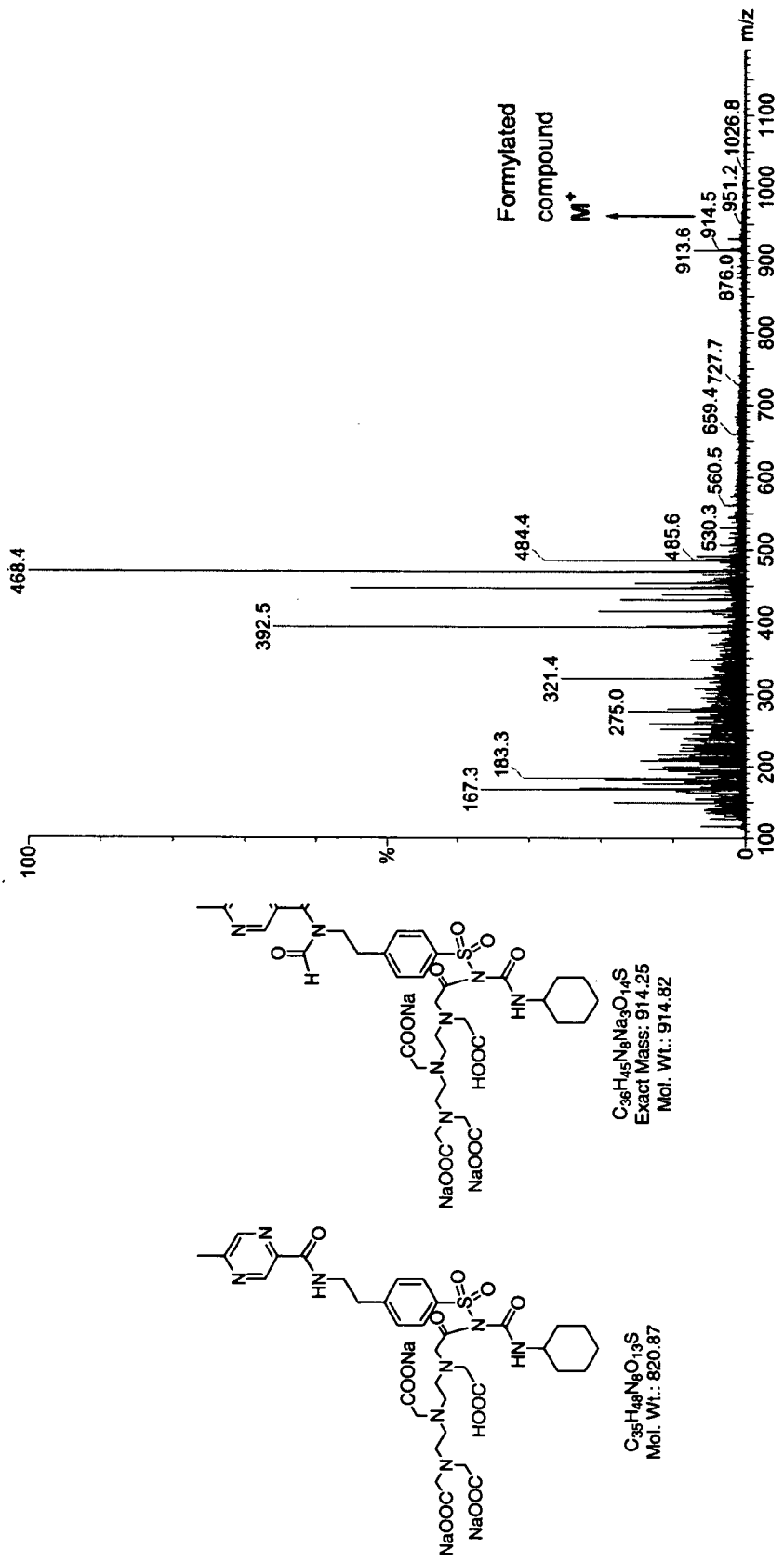
FIG. 17 is the Mass Spectrum of DTPA-Glipizide.

Glipizide (445.5 mg, 1.0 mmol) was dissolved in DMSO (anhydrous, 10 ml). Sodium amide (76.03 mg, 2.0 mmol) was then added. The reaction mixture was stirred at room temperature for 10 min. DTPA-dianhydride (357.32 mg, 1.0 mmol) was dissolved in DMSO (anhydrous, 10 ml). Sodium amide (76.03 mg, 2.0 mmol) was then added. The reaction mixture was stirred at room temperature for 10 min. DTPA-dianhydride (357.32 mg, 1.0 mmol) dissolved in 5 ml DMSO (anhydrous) was added and the mixture was stirred for 4 hours. The mixture was added with water (10 mL), followed by 1N-sodium hydroxide solution (3 mL) and stirred for 2 hours. The solid was filtered and washed with water. This recovered starting material was 142.6 mg (32%) after drying under vacuum. The aqueous phase was dialyzed with membrane (MW CO<500) for 2 days. DTPA-GLP (506.6 mg, 61.7% yield) as a white solid was gathered after lyophilization. The synthetic scheme is shown in FIG. 8. FIGS. 9-17 showed $^1$H-, $^{13}$C-NMR spectrum and assignment and mass spectrometry of DTPA-glipizide.

Example 3

Synthesis of DTPA-Glyburide (DTPA-GLB)

Figure 18:
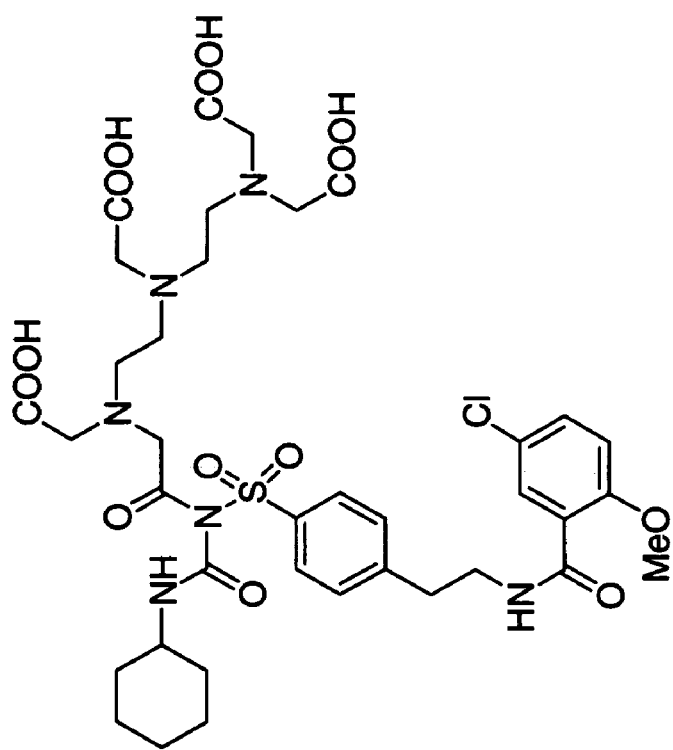
FIG. 18 is a synthetic scheme for DTPA-Glyburide.
Figure 18:
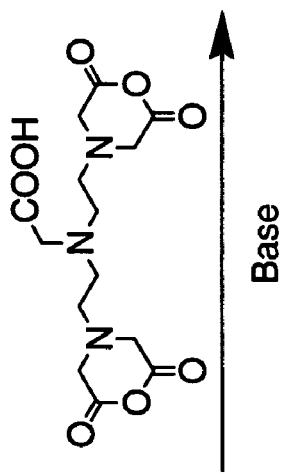
Figure 18:
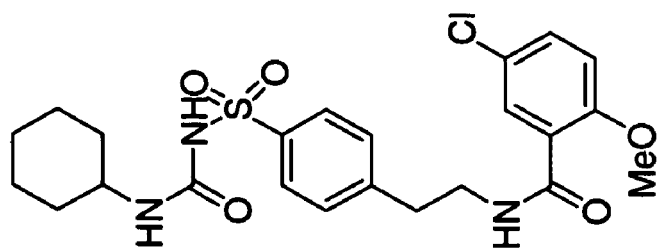
Figure 19:
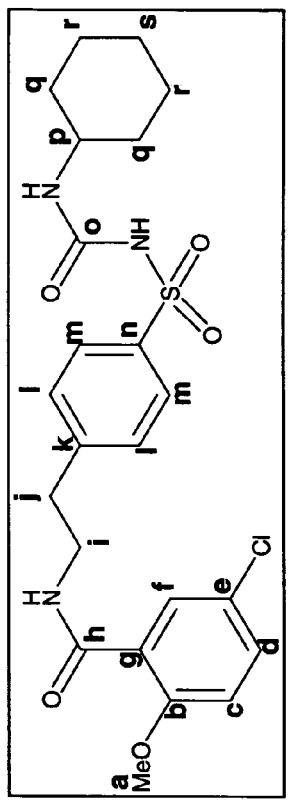
FIG. 19 is the $^1$H-NMR data of Glyburide.
Figure 20:
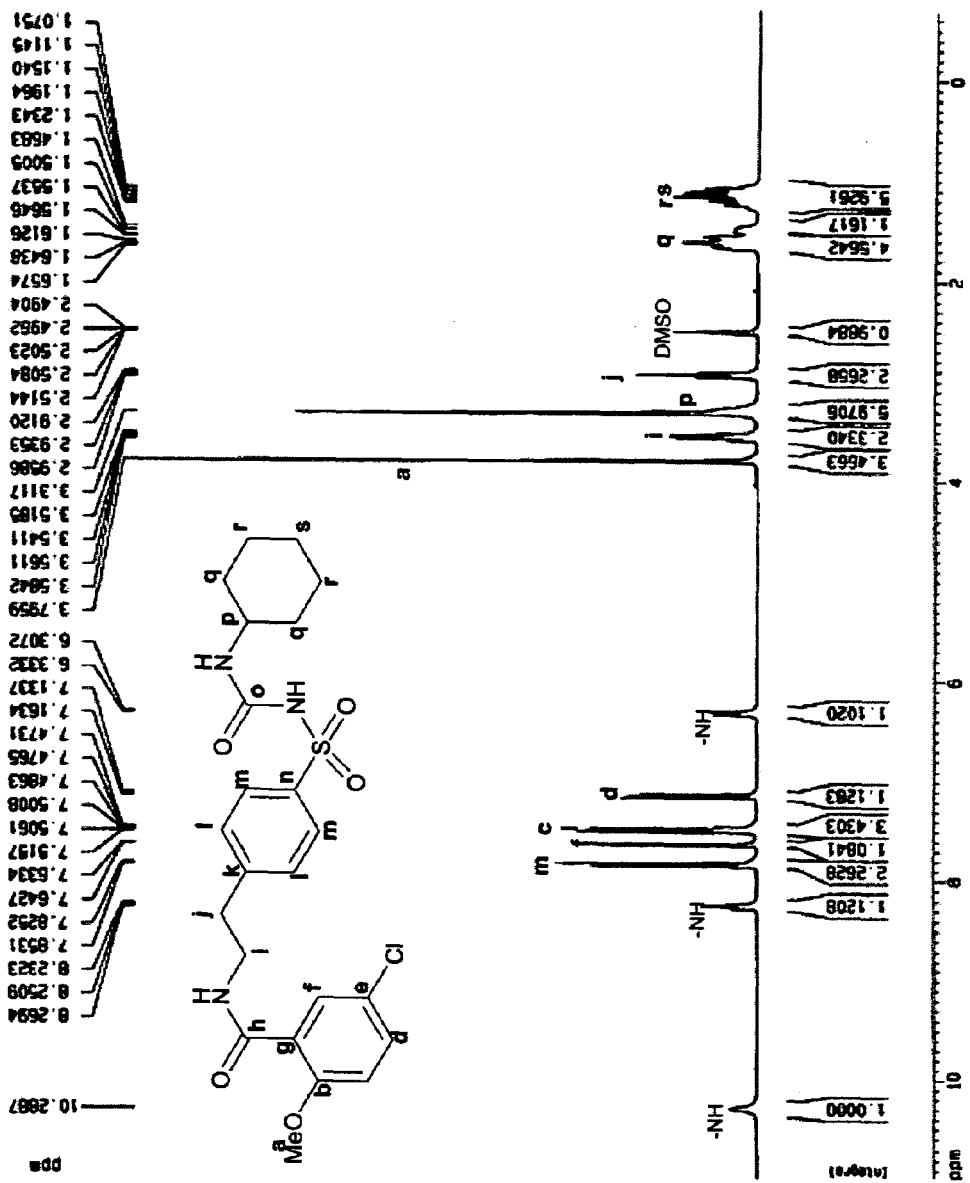
FIG. 20 is the $^1$H-NMR spectrum of Glyburide.
Figure 21:
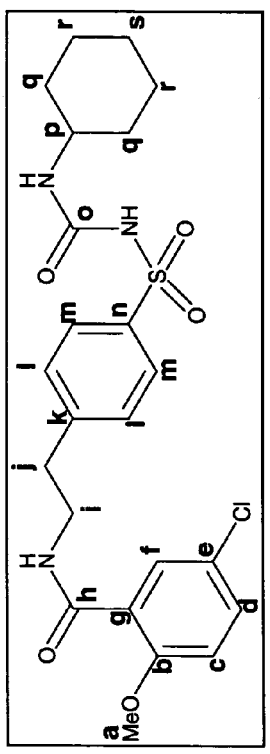
FIG. 21 is the $^{13}$C-NMR data of Glyburide.
Figure 22:
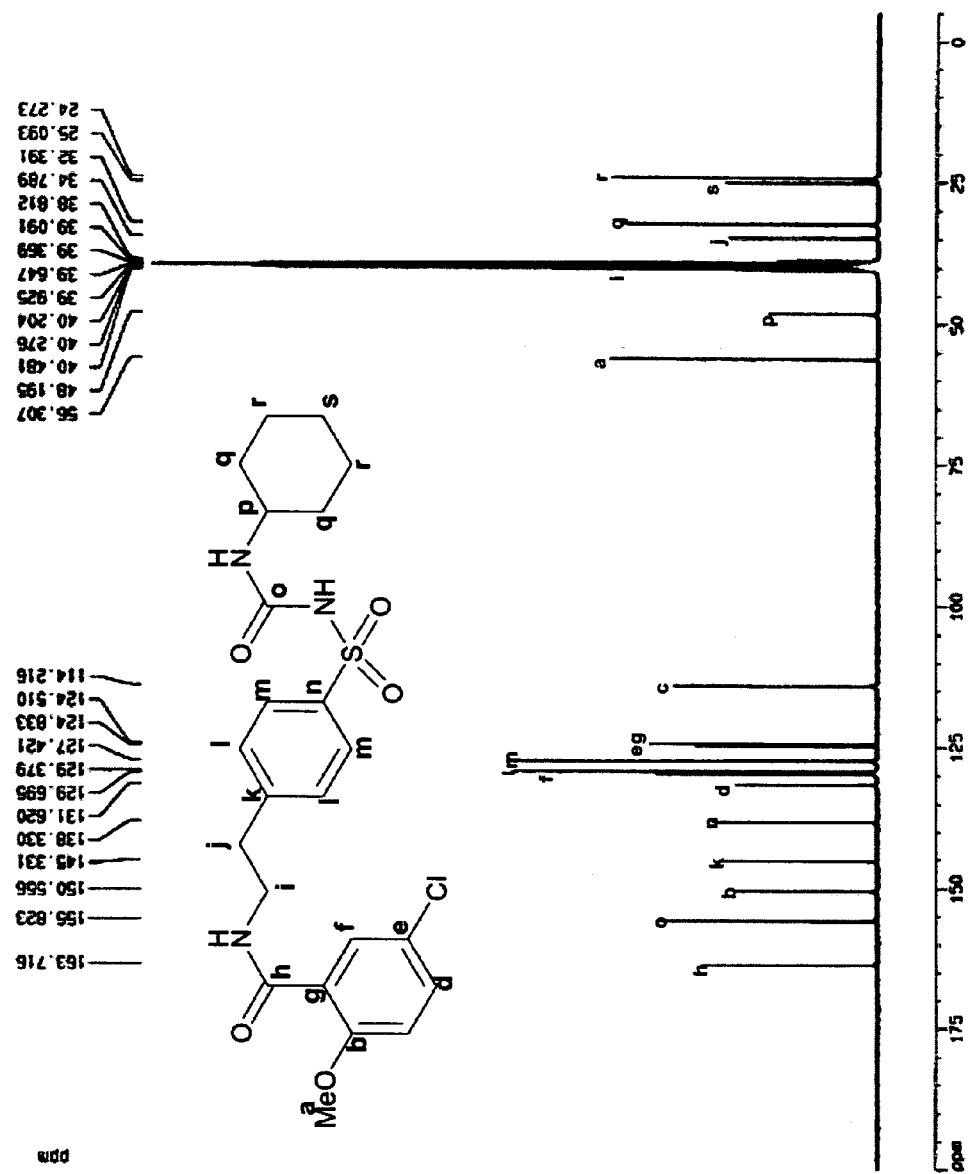
FIG. 22 is the $^{13}$C-NMR spectrum of Glyburide.
Figure 23:
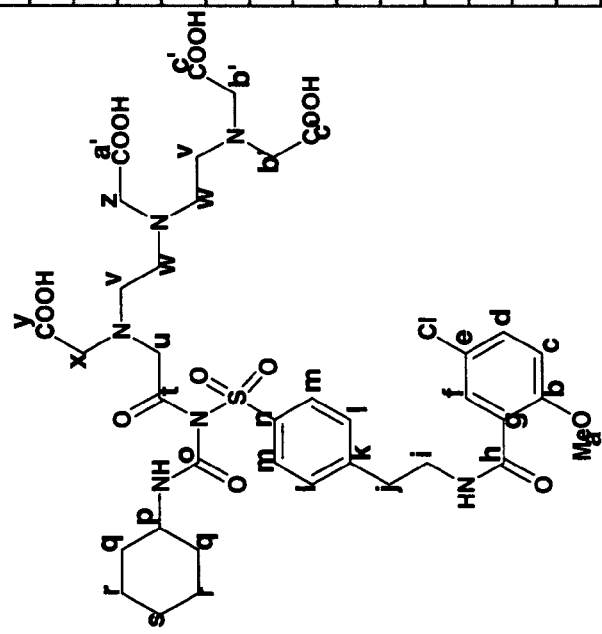
FIG. 23 is the $^1$H-NMR data of DTPA-Glyburide.
Figure 24:
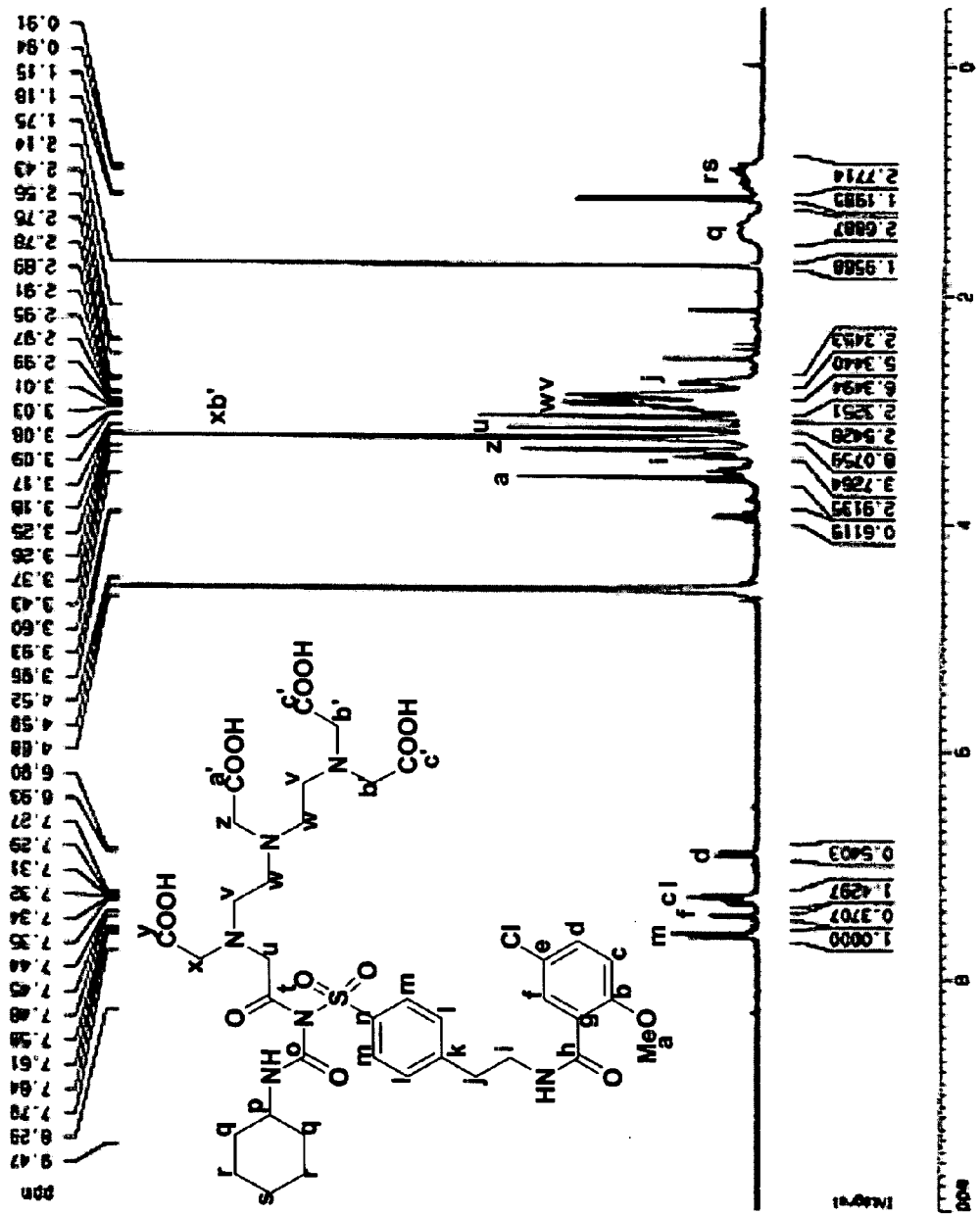
FIG. 24 is the $^1$H-NMR spectrum of DTPA-Glyburide.
Figure 25:
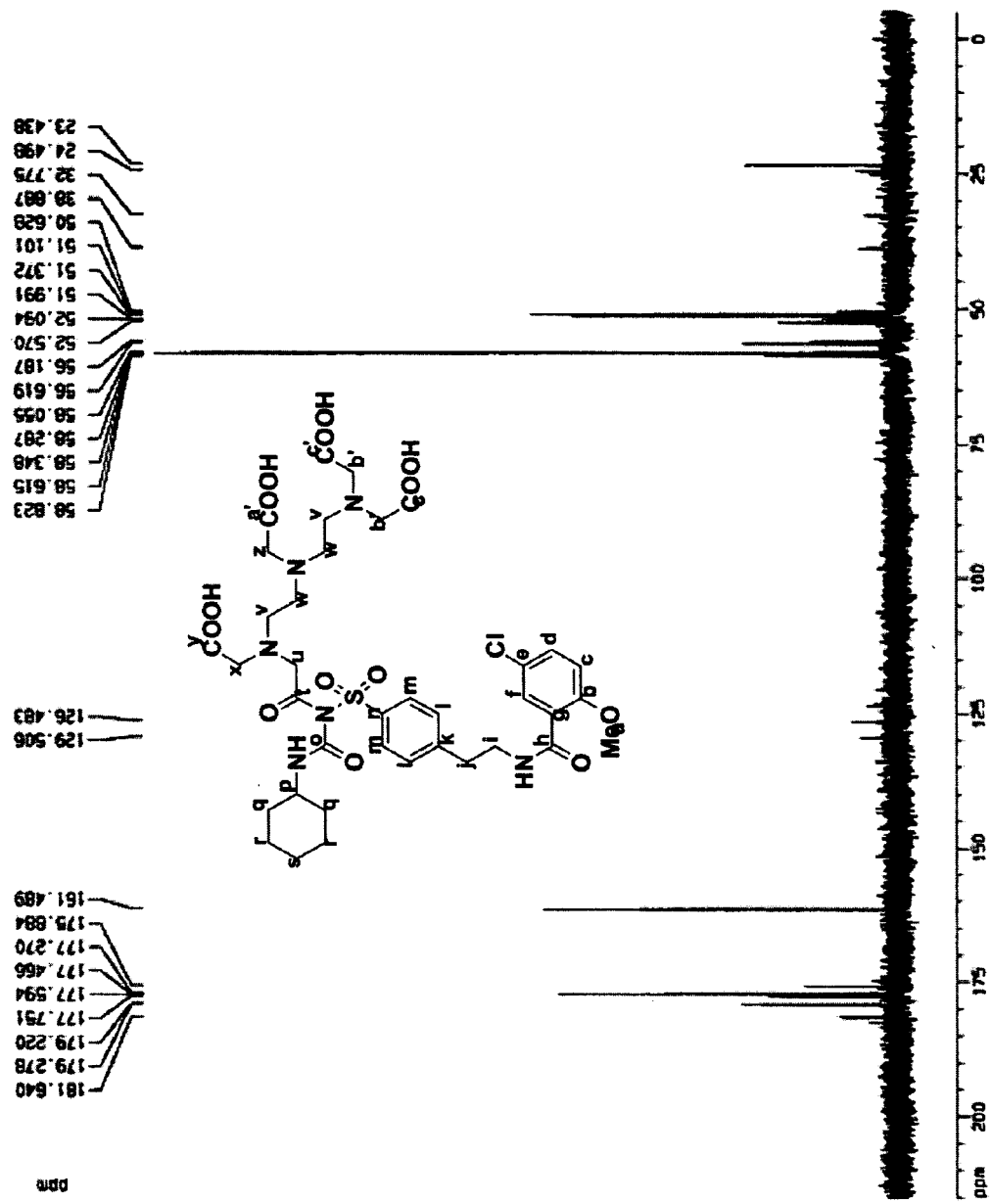
FIG. 25 is the $^{13}$C-NMR spectrum of DTPA-Glyburide.
Figure 26:
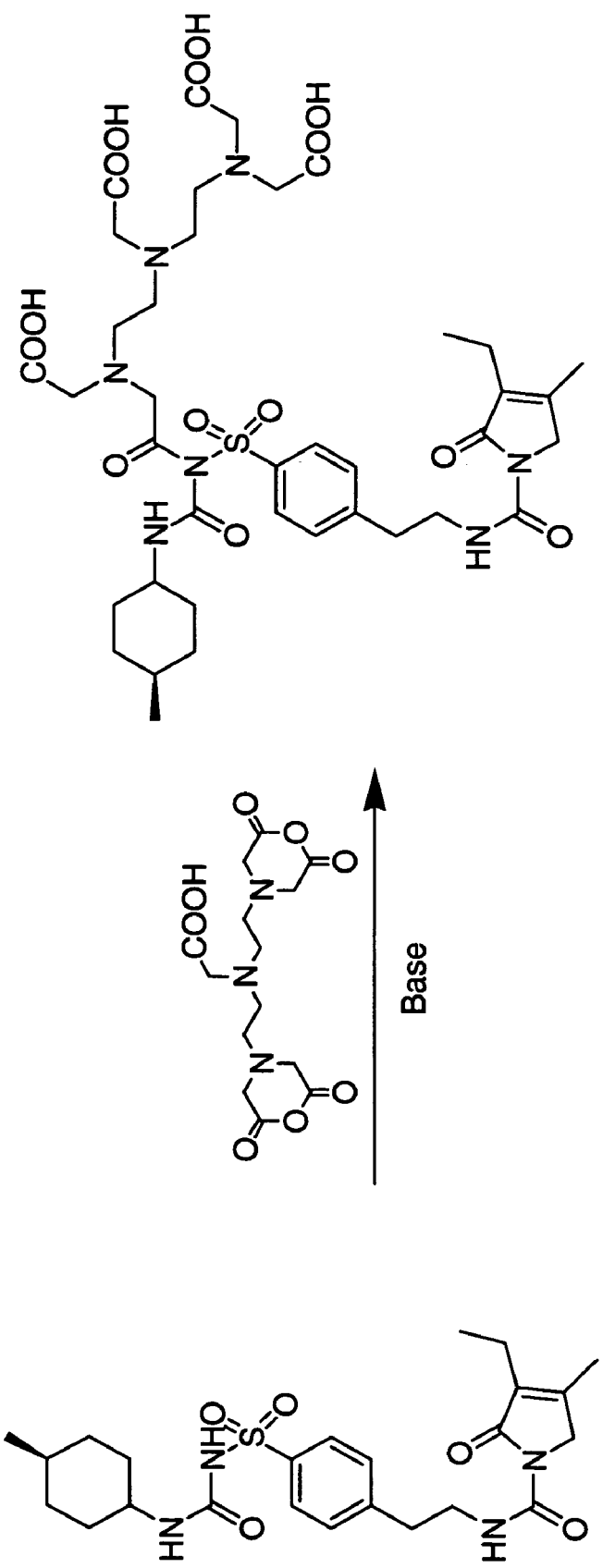
FIG. 26 is a synthetic scheme for DTPA-GLMP.

Glyburide (494.0 mg, 1.0 mmol) was dissolved in DMSO (anhydrous, 5 ml). Sodium amide (195.0 mg, 5.0 mmol) was then added. The reaction mixture was stirred at room temperature for 10 min. DTPA-dianhydride (357.32 mg, 1.0 mmol) dissolved in 5 ml DMSO (anhydrous) was added and the mixture was stirred for 22 hours. The dark green colored mixture was added with water (10 mL), followed by 1N-sodium hydroxide solution (5 mL) and stirred for 2 hours. The solid was filtered and washed with water. This recovered starting material was 88.9 mg (18%) after drying under vacuum. The aqueous phase was dialyzed with membrane (MW CO<500) for 2 days. DTPA-LB (695.5 mg, 80% yield) as a white solid was gathered after lyophilization. The synthetic scheme is shown in FIG. 18. FIGS. 19-25 showed $^1$H-, $^{13}$C-NMR spectrum and assignment of glyburide and DTPA-glyburide.

Example 4

Synthesis of DTPA-Glimepiride (DTPA-GLMP)

Figure 27:
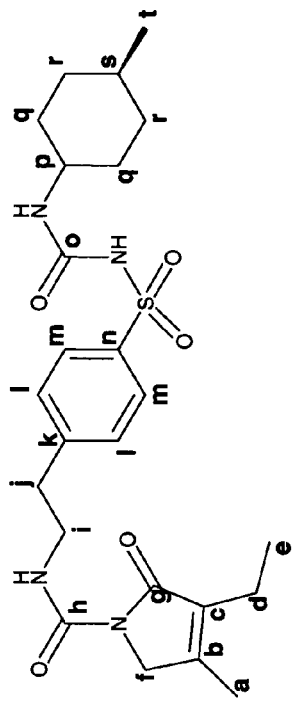
FIG. 27 is $^1$H-NMR data of GLMP.
Figure 28:
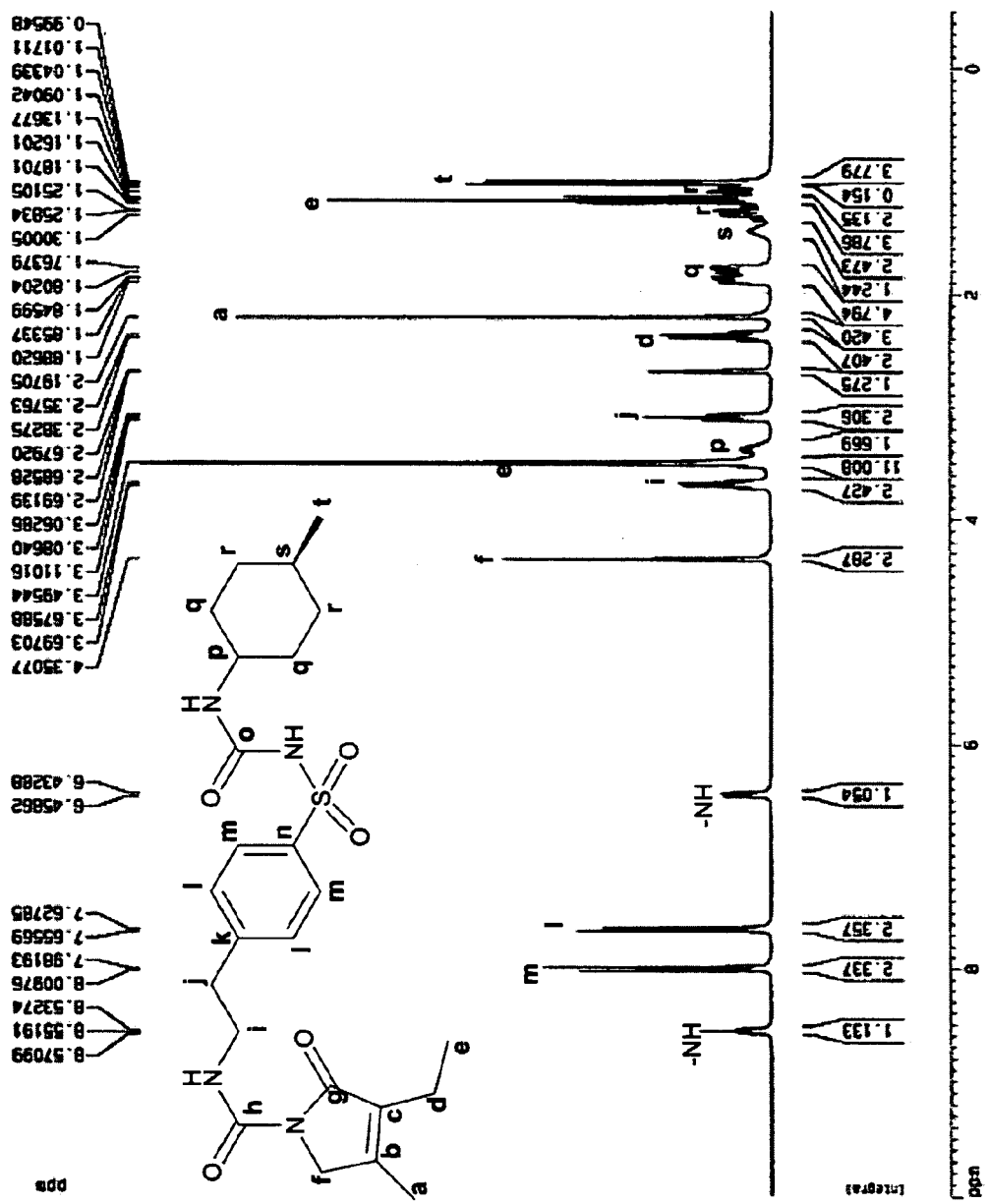
FIG. 28 is a $^1$H-NMR spectrum of GLMP.
Figure 29:
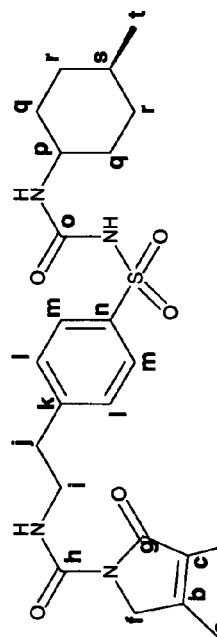
FIG. 29 is $^{13}$C-NMR data of GLMP.
Figure 30:
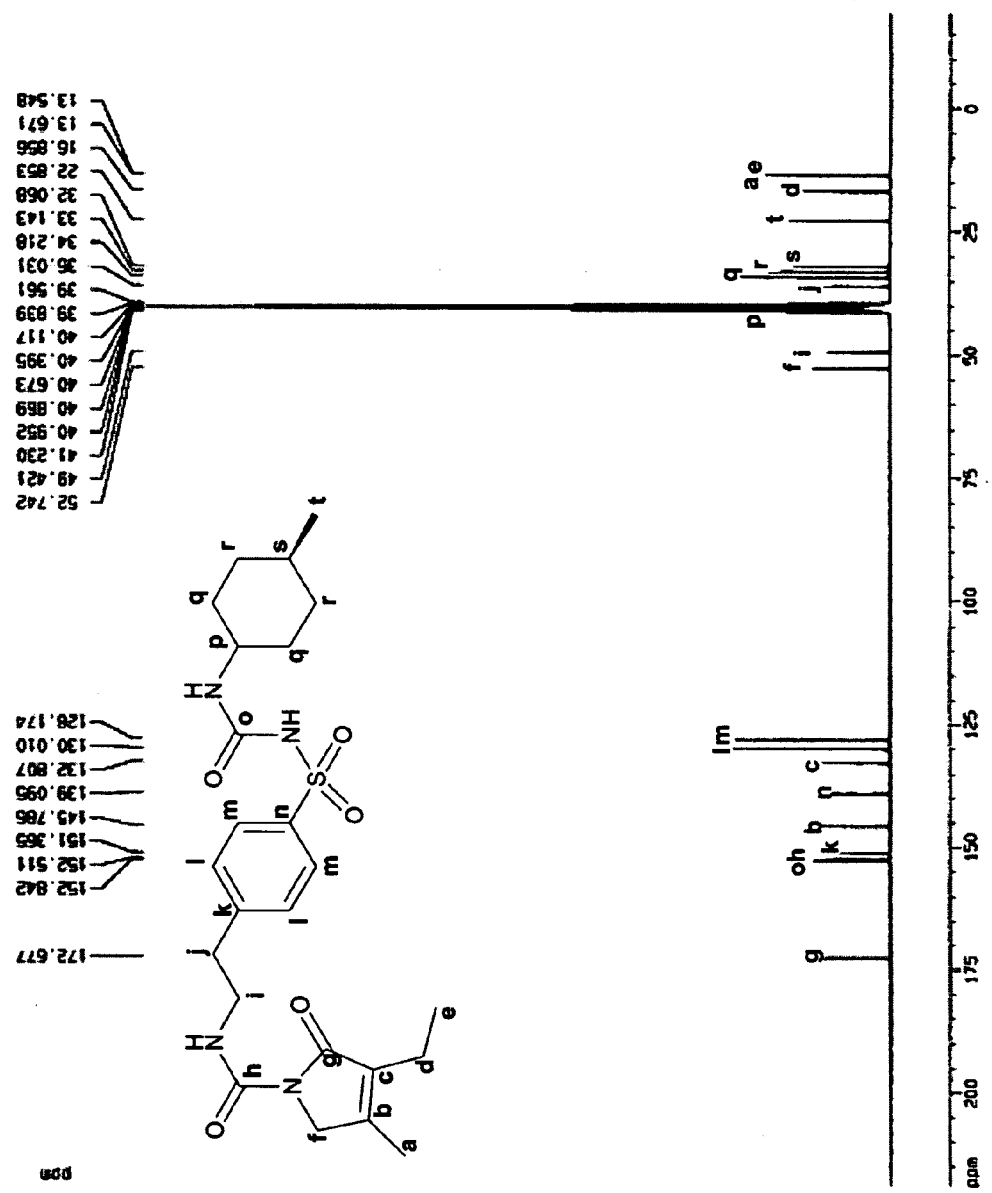
FIG. 30 is a $^{13}$C-NMR spectrum of GLMP.
Figure 31:
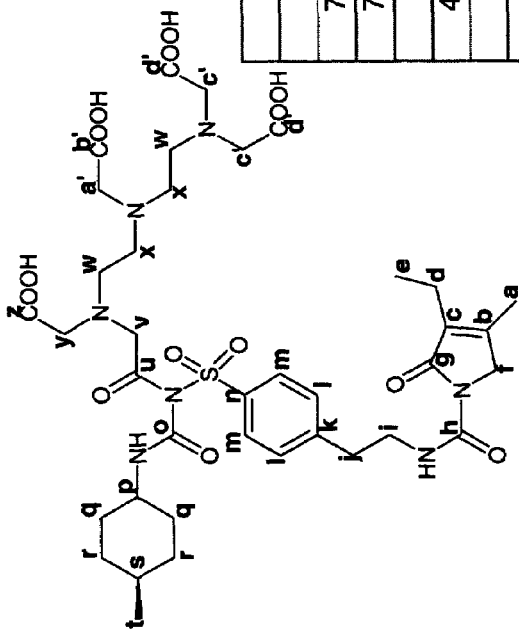
FIG. 31 is $^1$H-NMR data of DTPA-GLMP.
Figure 32:
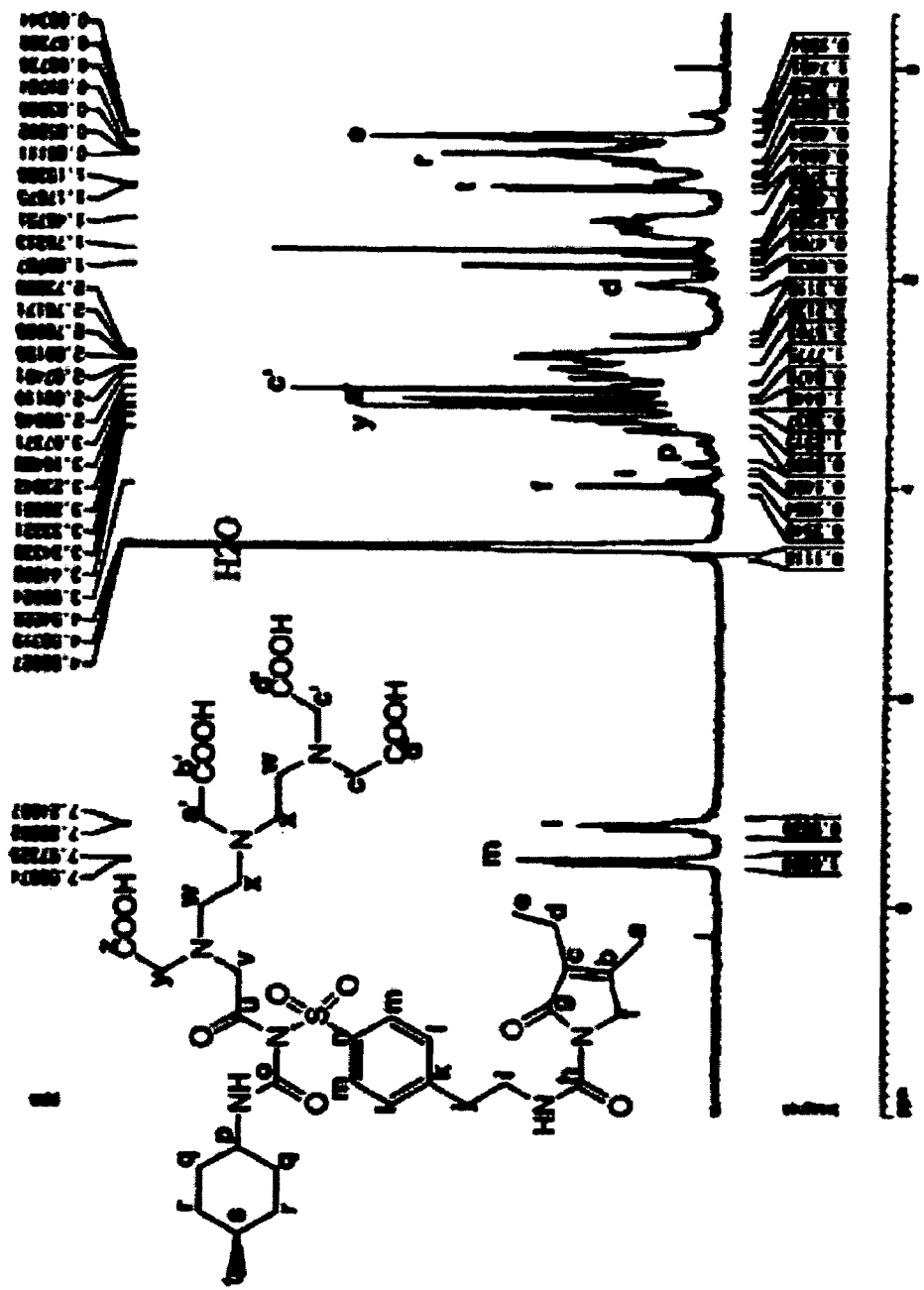
FIG. 32 is a $^1$H-NMR spectrum of DTPA-GLMP.
Figure 33:
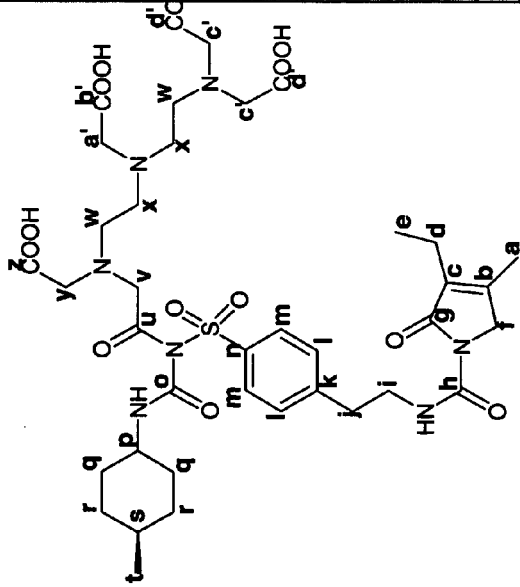
FIG. 33 is $^{13}$C-NMR data of DTPA-GLMP.
Figure 34:
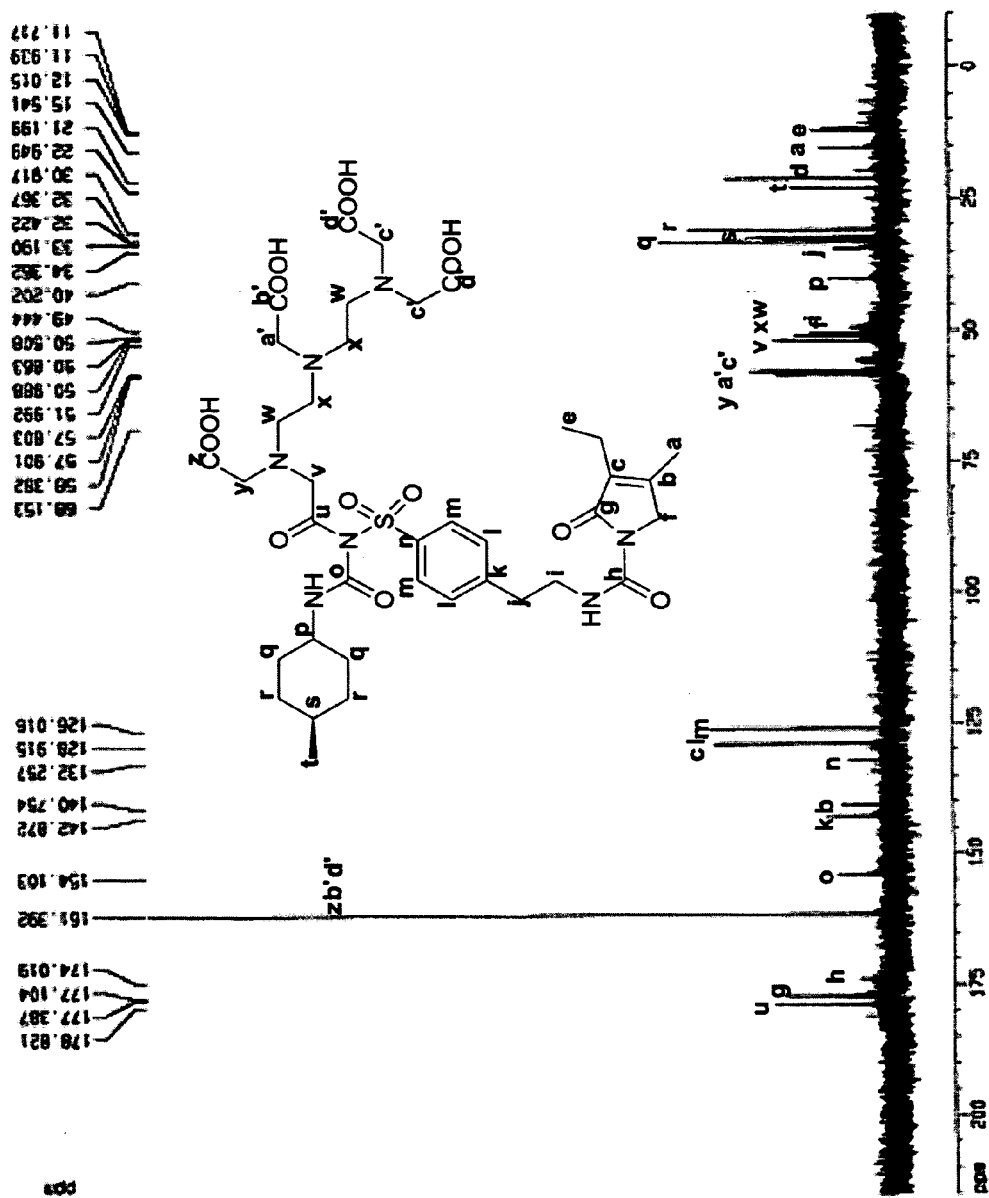
FIG. 34 is a $^{13}$C-NMR spectrum of DTPA-GLMP.

Glimepiride (490.6 mg, 1.0 mmol) was dissolved in DMSO (anhydrous, 10 ml). Sodium amide (195.0 mg, 5.0 mmol) was then added. The reaction mixture was stirred at room temperature for 10 min. DTPA-dianhydride (357.32 mg, 1.0 mmol) dissolved in 5 ml DMSO (anhydrous) was added and the mixture was stirred for 18 hours. The dark brown colored mixture was added with water (10 mL), followed by 1N-sodium hydroxide solution (5 mL) and stirred for 2 hours. The solid was filtered and washed with water. The aqueous phase was dialyzed with membrane (MW CO<500) for 2 days. DTPA-GLMP (782.3 mg, 90.3% yield) was a white solid was gathered after lyophilization. The synthetic scheme is shown in FIG. 27. FIGS. 28-34 showed 1H-, $^{13}$C-NMR spectrum and assignment of glimepiride and DTPA-glimepiride.

Example 5

Radiolabel DTPA-Antidiabetic Conjugates

Figure 35:
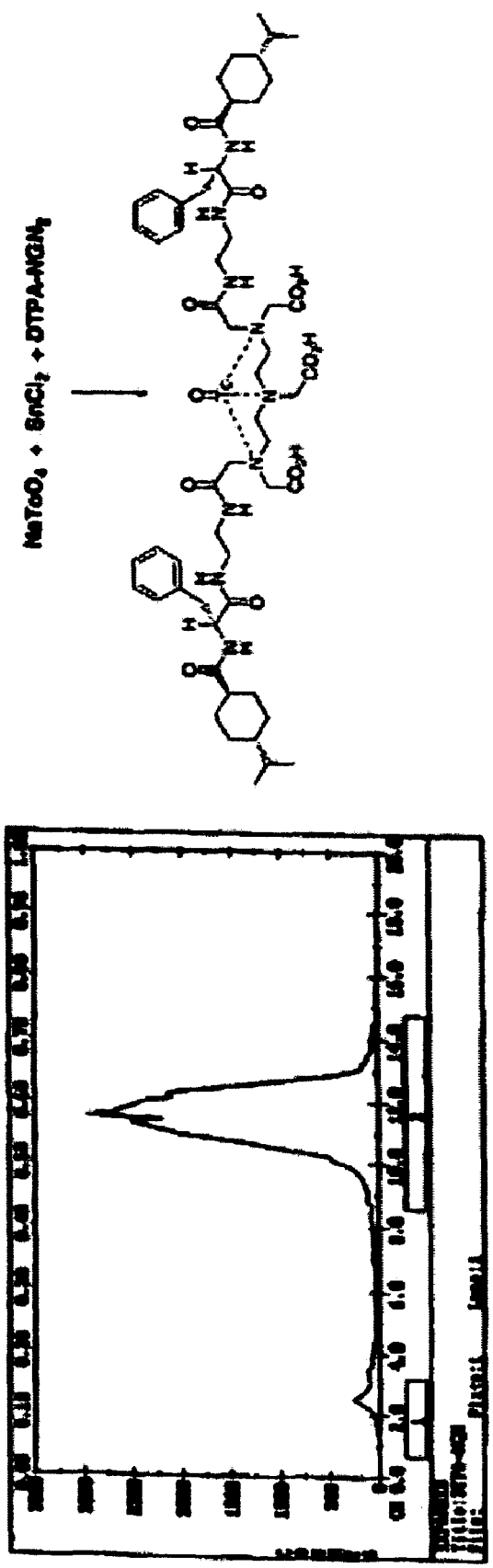
FIG. 35 is ITLC data for Tc-DTPA-NGN2.
Figure 36:
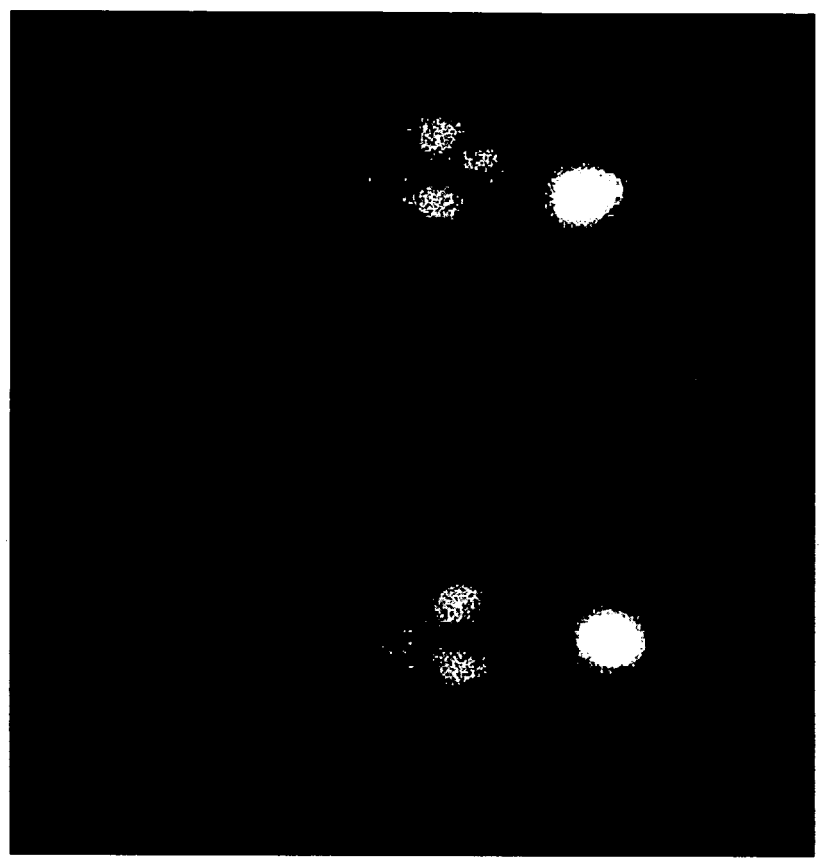
FIG. 36 is nuclear imaging of $^{99m}$Tc-DTPA-Nateglinide. Mammary tumor-bearing rats were imaged with $^{99m}$Tc-DTPA (left panel) and $^{99m}$Tc-DTPA-NGN2 (right panel) (300 μCi, i.v.). Selected planar images of $^{99m}$Tc-DTPA-NGN2 are presented at 5 and 50 minutes post-injection. The arrow indicates the pancreas.
Figure 36:
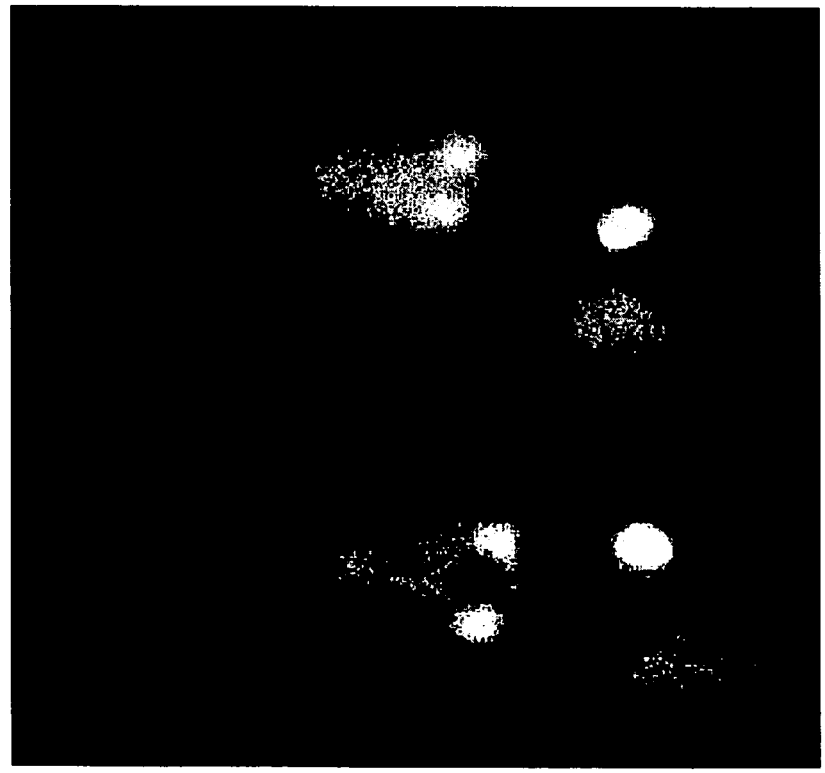
Figure 37:
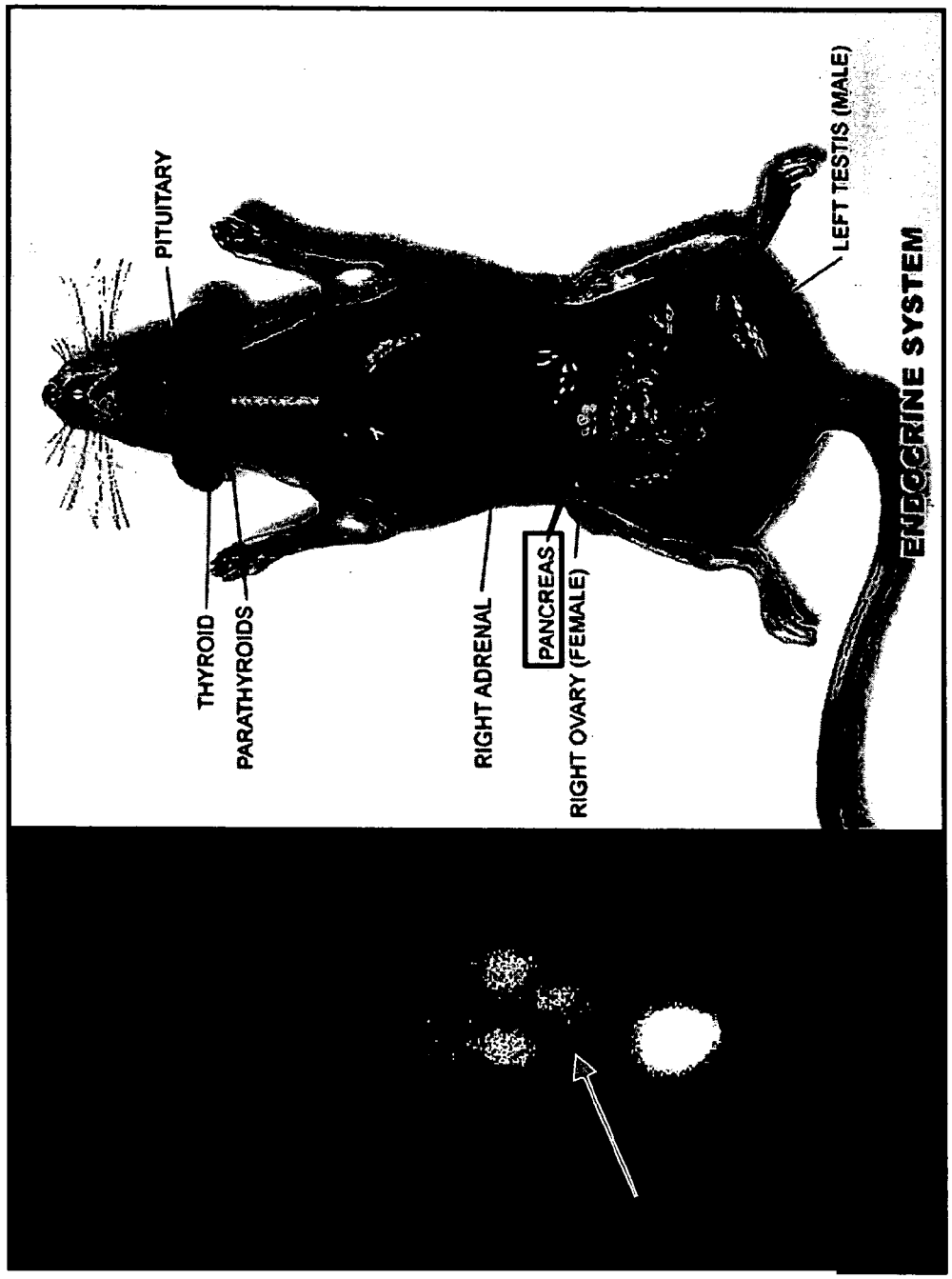
FIG. 37 is an image of a mammary tumor-bearing rat imaged with $^{99m}$Tc-DTPA-NGN2 (300 μCi, i.v.) Selected planar images of $^{99m}$Tc-DTPA-NGN2 are presented at 50 minutes post-injection. The arrow indicates the pancreas.
Figure 38:
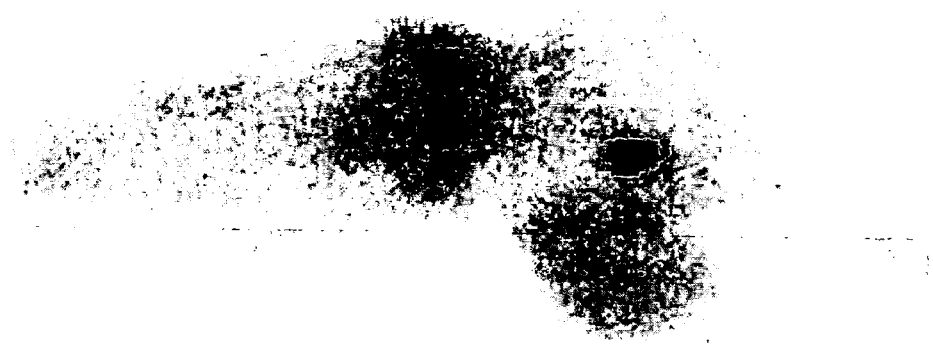
FIG. 38 is planar scintigraphy images of $^{99m}$Tc-DTPA in 13762 tumor-bearing rats (300 μCi/rat, i.v. injection).
Figure 38:
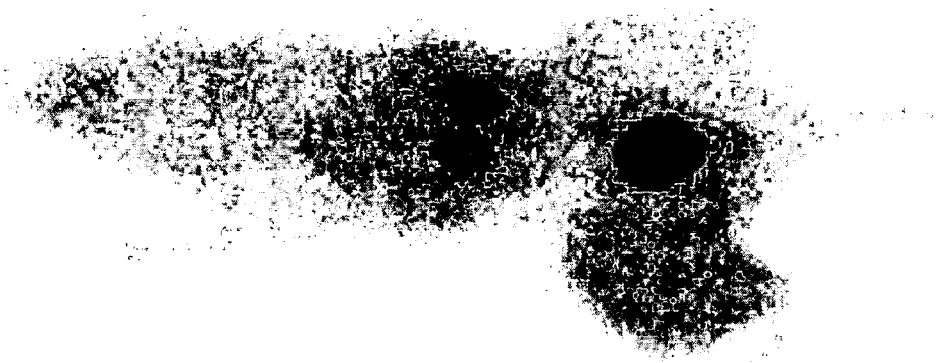
Figure 38:
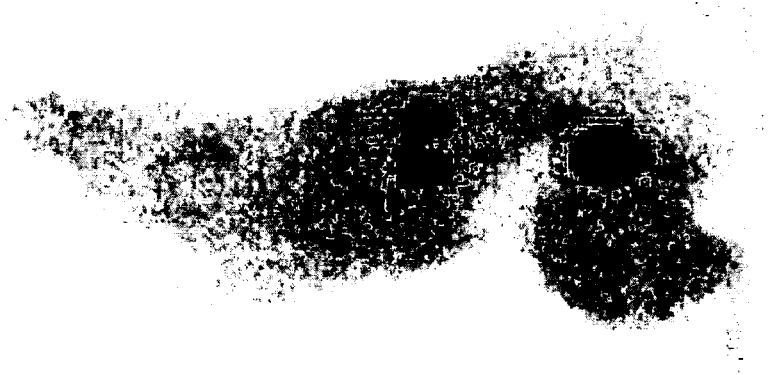
Figure 39:
FIG. 39 is planar scintigraphy images of $^{99m}$Tc-DTPA-NGN (2) in 13762 tumor-bearing rats (300 μCi/rat, i.v. injection).
Figure 40:
FIG. 40 is planar scintigraphy images of $^{99m}$Tc-DTPA-NGN (1) in 13762 tumor-bearing rats (300 μCi/rat, i.v. injection).
Figure 41:
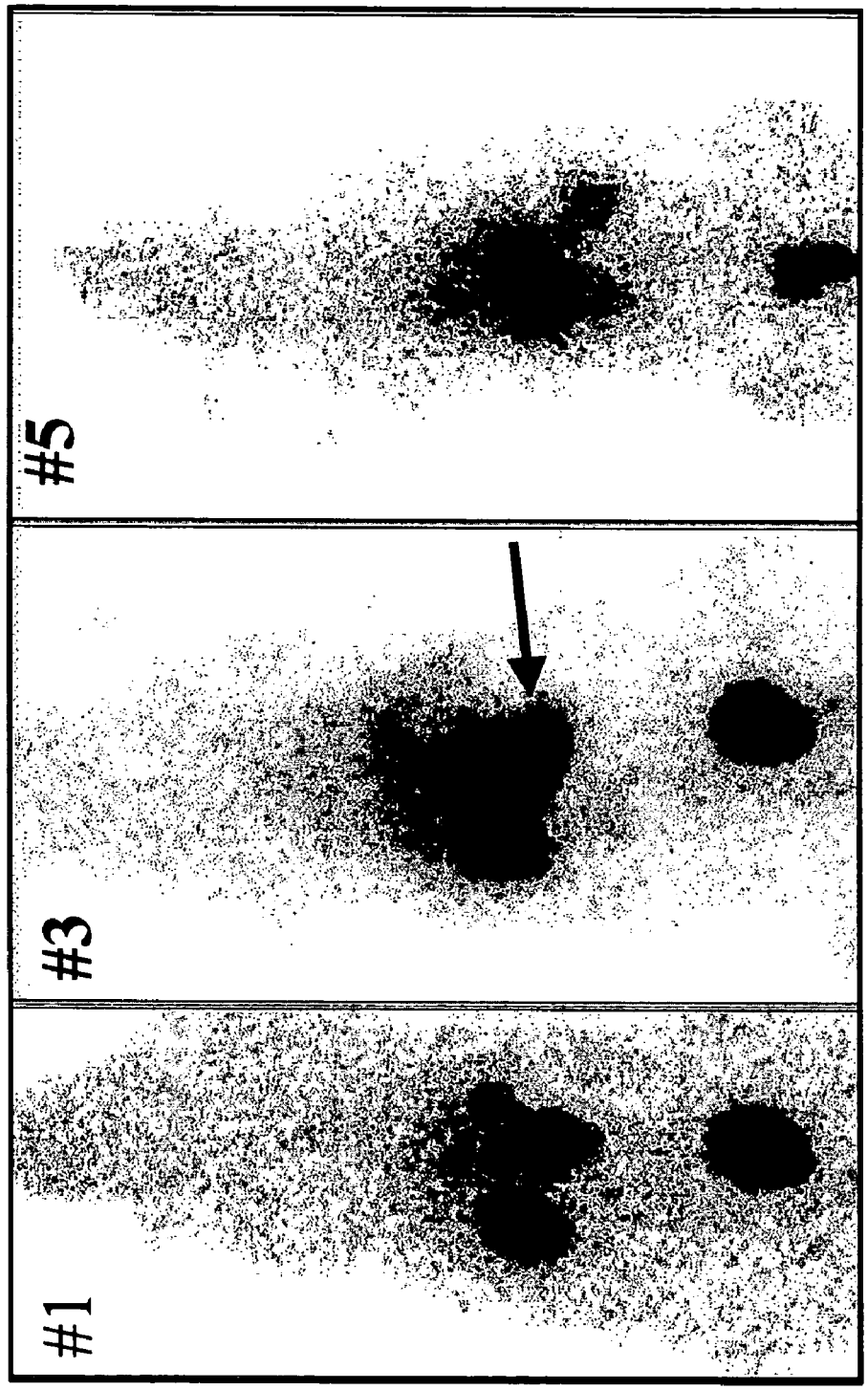
FIG. 41 is images of breast tumor bearing rats imaged with $^{99m}$Tc-DTPA (left panel), $^{99m}$Tc-DTPA-NGN2 (middle panel) and $^{99m}$Tc-DTPA-NGN2 with a blocking dose of 4 mg/kg NGN2 (right panel) (300 μCi, i.v.). Selected planar images are shown at 150 minutes post-injection.
Figure 42:
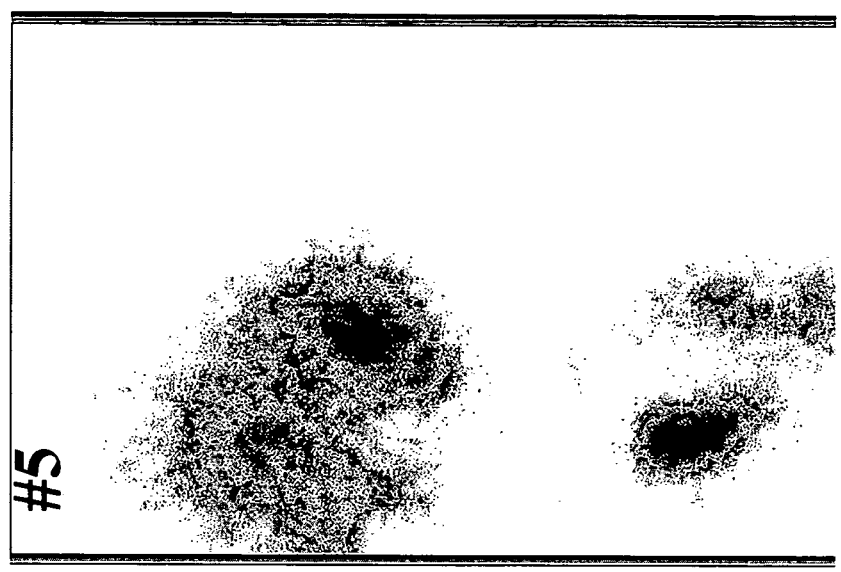
FIG. 42 is images of breast tumor bearing rats imaged with $^{99m}$Tc-DTPA (left panel), $^{99m}$Tc-DTPA-NGN2 (middle panel) and $^{99m}$Tc-DTPA-NGN2 with a blocking dose of 4 mg/kg NGN2 (right panel) (300 μCi, i.v.). Selected planar images are shown at 150 minutes post-injection. The arrow indicates the pancreas.
Figure 42:
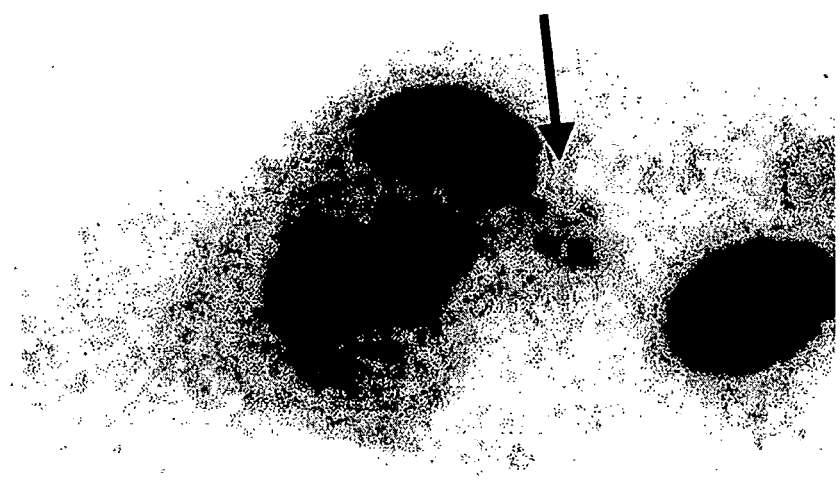
Figure 42:
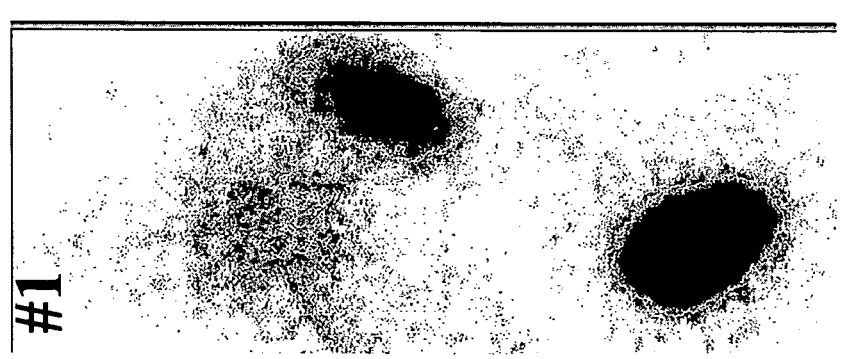
Figure 43:
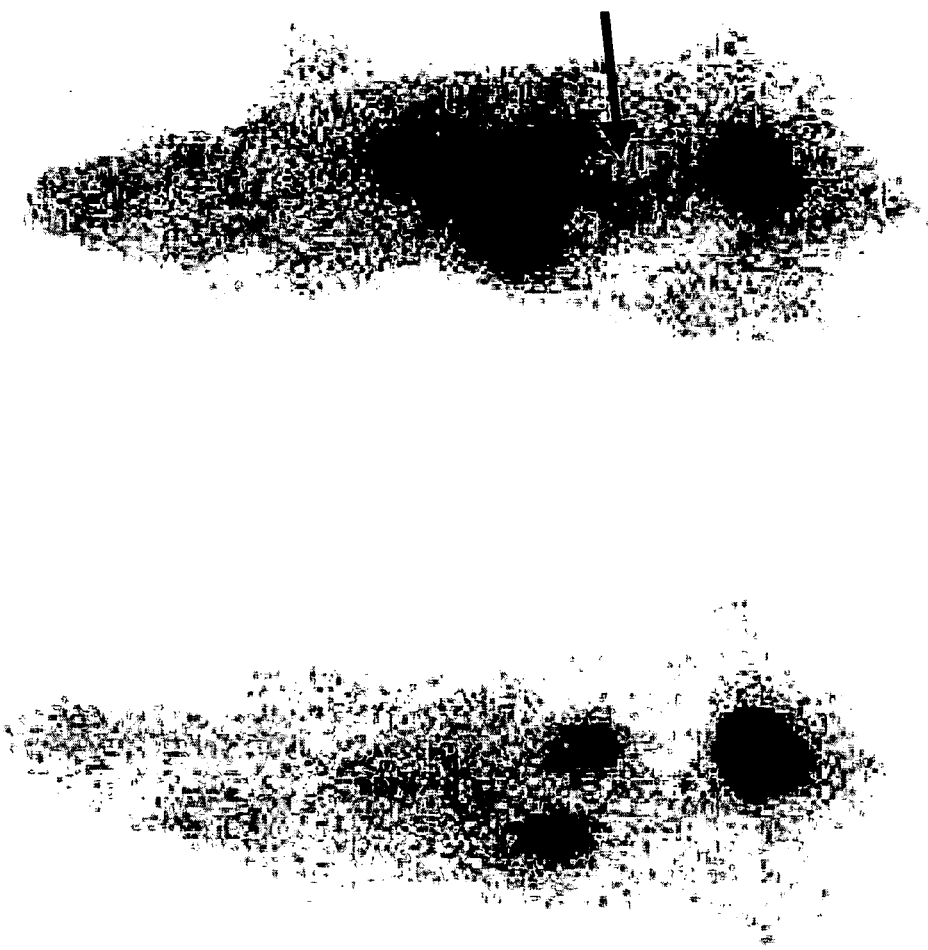
FIG. 43 is planar scintigraphy images of $^{99m}$Tc-DTPA and $^{99m}$Tc-DTPA-Glipizide (GLUCOTROL) in rats (300 μCi/rat, i.v. injection) at 5 minutes post injection.
Figure 44:
FIG. 44 is planar scintigraphy images of $^{99m}$Tc-DTPA and $^{99m}$Tc-DTPA-Glipizide (GLUCOTROL) in rats (300 μCi/rat, i.v. injection) at 15 minutes post injection.

Radiosynthesis of $^{99m}$Tc-DTPA-antidiabetic agents were achieved by adding the required amount of DTPA-antidiabetic agents (5-10 mg) and tin (II) chloride (SnCl$_2$, 100$_{\mu g}$) and pertechnetate (Na$^{99m}$TcO$_4$, 5 mCi). Radiochemical purity was assessed by radio-TLC (Bioscan, Washington, D.C.) using 1 M ammonium acetate: methanol (4:1) as an eluant. High-performance liquid chromatography (HPLC), equipped with a NaI detector and UV detector (254 nm), was performed on a gel permeation column (Biosep SEC-S3000, 7.8×300 mm, Phenomenex, Torrance Calif.) using a flow rate of 1.0 m/min. The eluant was 0.1% LiBr in phosphate buffered saline (PBS 10 mM, pH=7.4). Radiochemical purity was <96% for all four agents. Radio-TLC data of $^{99m}$Tc-DTPA-nateglinide is shown in FIG. 35.

Example 6

Scintigraphic Imaging

Scintigraphic imaging in rodents was conducted as follows:

Female Fischer 344 rates (150-175 g) (Harlan Sprague-Dawley, Inc., Indianapolis, Ind.) were inoculated subcutaneously in the right leg with breast cancer cells (10$^6$ cells/rat) from the 13762 NF cell line (known as DMBA-induced breast cancer cell line). Scintigraphic imaging was serially performed on day 14 after inoculation. Planar images were obtained at 0.5, 1 and 2 hours after injection of 300 μCi of $^{99m}$Tc-DTPA-NGN or $^{99m}$Tc-DTPA-GLP via tail vein. Control groups were given $^{99m}$Tc-DTPA. Imaging was conducted with a gamma camera from Digirad (2020tc Imager, San Diego, Calif.) equipped with a low-energy parallel-hole collimator. The field of view is 20 cm×20 cm with an edge of 1.3 cm. The intrinsic spatial resolution is 3 mm and the matrix is 64×64. The system is designed for a planar image with sensitivity of 56 counts/second (cps)/MBq and spatial resolution of 7.6 mm. FIGS. 36-44 showed that pancreas could be visualized with either $^{99m}$Tc-DTPA-nateglinide (NGN) or $^{99m}$Tc-DTPA-glipizide in normal rat and tumor-bearing rats.

Figure 45:
FIG. 45 is planar scintigraphy images of $^{99m}$Tc-DTPA in VX2 tumor-bearing rabbits (1 mCi/rabbit, i.v. injection).
Figure 46:
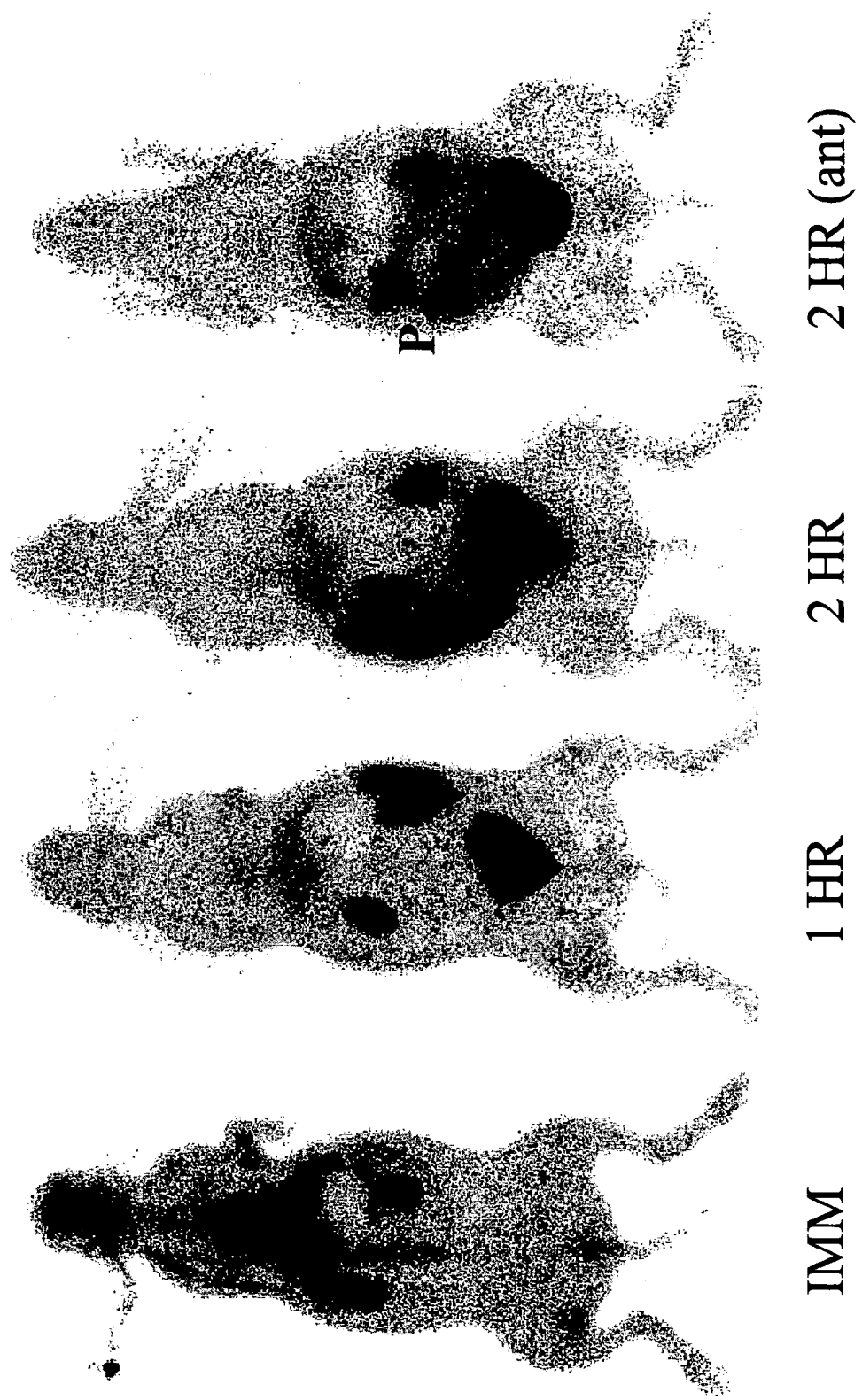
FIG. 46 is planar scintigraphy images of $^{99m}$Tc-DTPA-NGN in VX2 tumor-bearing rabbits (1 mCi/rabbit, i.v. injection). P indicates the pancreas.
Figure 47:
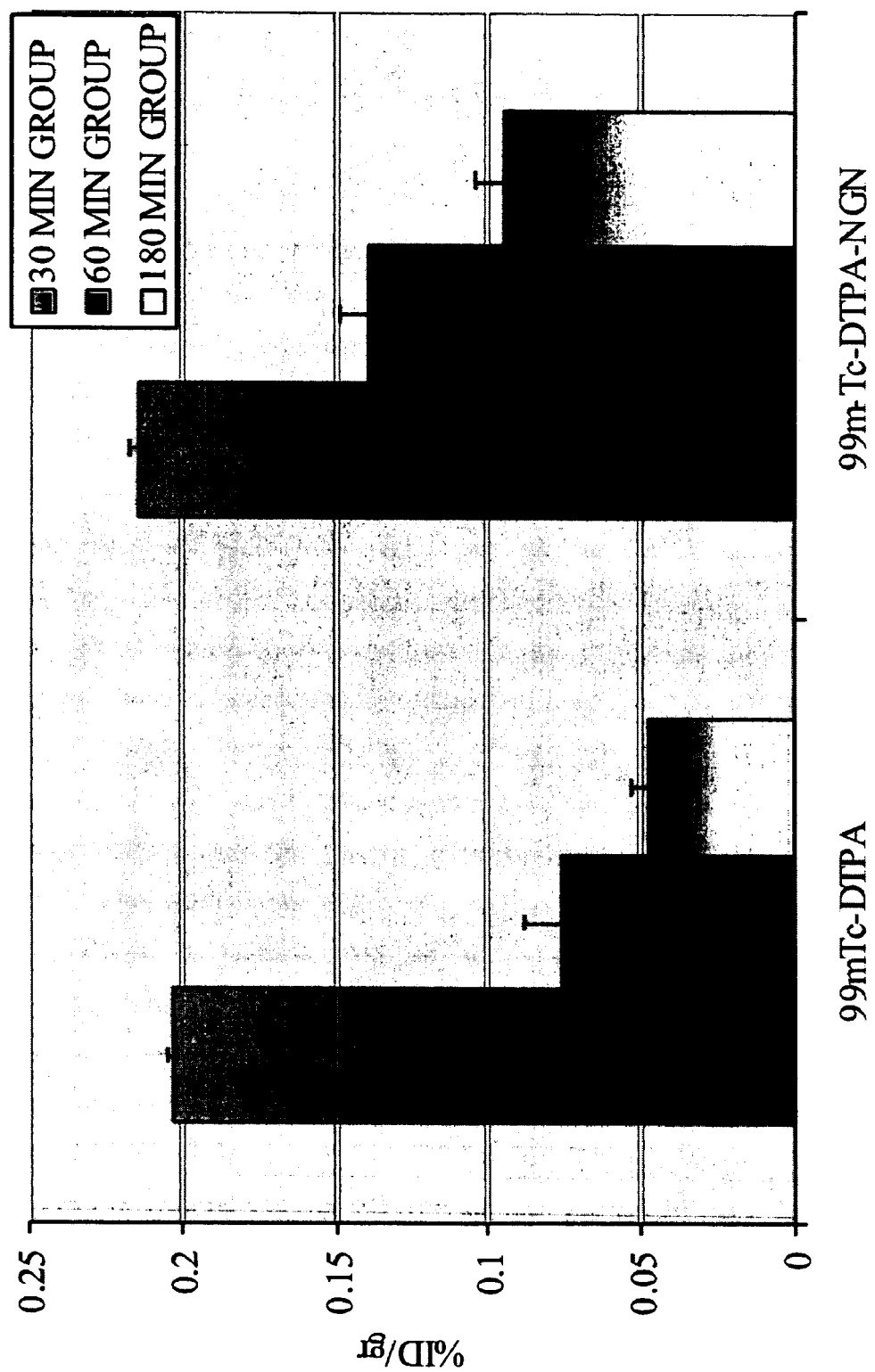
FIG. 47 is a graphical representation comparing pancreas uptake for $^{99m}$Tc-DTPA and $^{99m}$Tc-DTPA-NGN in breast tumor-bearing rats (n=3/time interval, 20 μCi, IV, p=0.11, 0.05, and 0.01).
Figure 48:
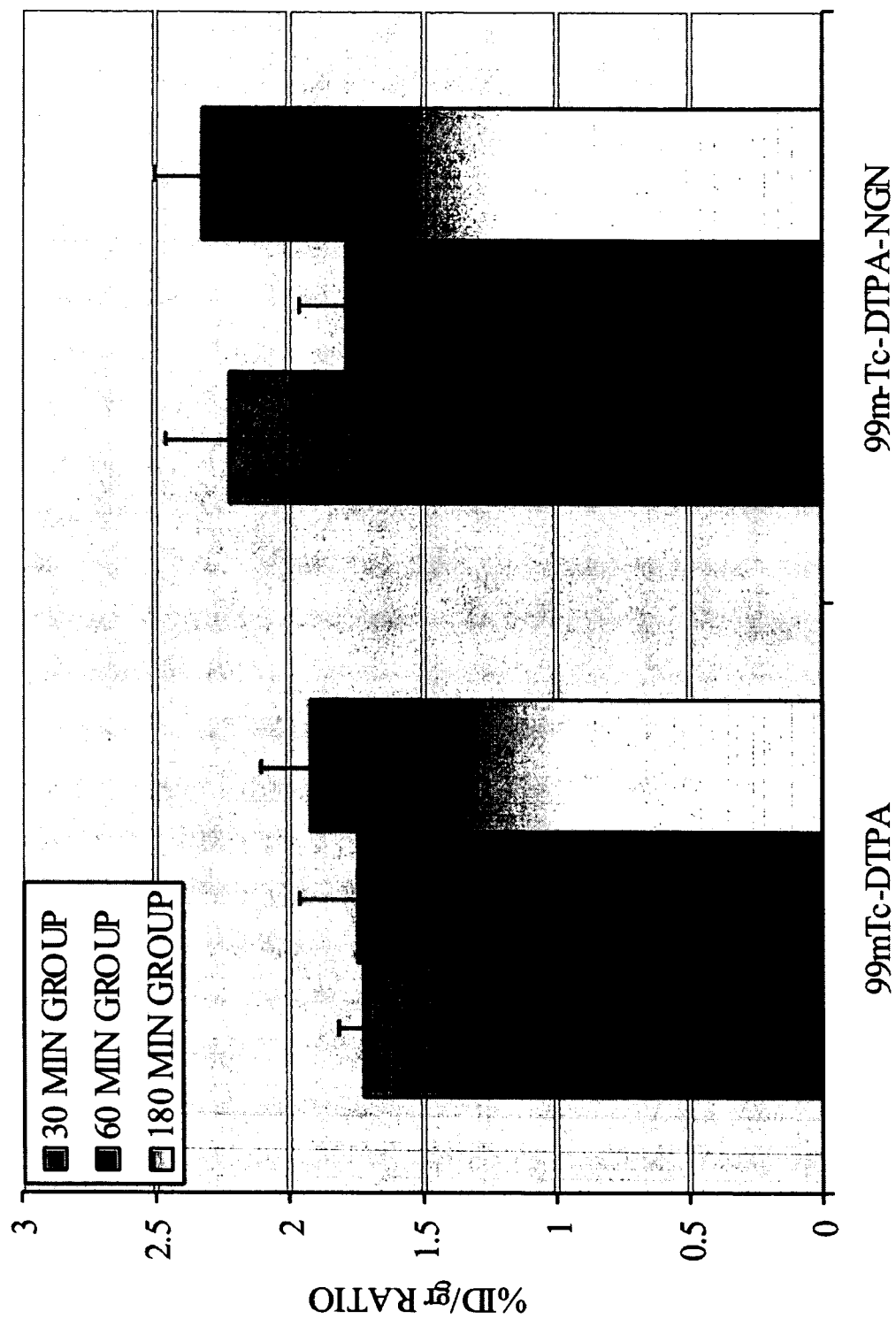
FIG. 48 is a graphical representation of pancreas to muscle count density ratio of $^{99m}$Tc-DTPA and $^{99m}$Tc-NGN in breast tumor bearing rats (n=3/time interval, μCi/rat, IV, p=0.19, 0.19, and 0.029).

Scintigraphic imaging in rabbits was conducted as follows:

Male (n=4) New Zealand white rabbits (Raynichols Rabbitry, Lumberton, Tex.) were inoculated with VX-2 cells (rabbit driven mammary squamous cell carcinoma). At day 14 post-inoculation, scintigraphic imaging studies were conducted with $^{99m}$Tc-DTPA-NGN (1 mCi, iv). Computer outlined region of interest was used to analyze target-to-nontarget ratios. FIGS. 45 and 46 showed that pancreas could be visualized with $^{99m}$Tc-DTPA-nateglinide (NGN). FIGS. 47 and 48 showed that pancreas uptake was higher than control groups.

In summary, the imaging data demonstrated that the pancreas can be imaged with radiolabeled nateglinide and glipizide. Thus, uptake changes in pancreas can be assessed using this specific molecular marker.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of monitoring pancreatic beta cell mass or morphology in a mammal comprising administering to the mammal a composition comprising diethylenetriamine pentaacetic acid (DTPA)-nateglinide, diethylenetriamine pentaacetic acid (DTPA)-glipizide, diethylenetriamine pentaacetic acid (DTPA)-glyburide or diethylenetriamine pentaacetic acid (DTPA)-glimepiride and a chelated metal ion and imaging the pancreas.

2. The method of claim 1, wherein the metal ion is a radionuclide.

3. The method of claim 1, wherein the metal ion is a beta emitter.

4. The method of claim 1, wherein the metal ion is a gamma emitter.

5. The method of claim 1, wherein the metal ion is $^{99m}$Tc, $^{60-64}$Cu, Gd, $^{166}$Ho, or $^{187, 188}$Re.

6. The method of claim 1, wherein the composition comprises $^{99m}$Tc-DTPA-nateglinide, $^{99m}$Tc-DTPA-glipizide, $^{99m}$Tc-DTPA-glyburide or $^{99m}$Tc-DTPA-glimepiride.

7. A method of monitoring pancreatic beta cell mass or morphology in a mammal comprising administering to the mammal a composition comprising $^{99m}$Tc-DTPA-glipizide and imaging the pancreas.

8. The method of claim 1, wherein the mammal is a human.

9. The method of claim 1, wherein the imaging comprises gamma imaging.

10. The method of claim 1, wherein the pancreas is imaged by scintigraphy or computed tomography.

* * * * *

UNITED STATES PATENT AND TRADEMARK OFFICE
CERTIFICATE OF CORRECTION

PATENT NO. : 7,611,693 B2
APPLICATION NO. : 10/942615
DATED : November 3, 2009
INVENTOR(S) : David J. Yang et al.

Page 1 of 1

It is certified that error appears in the above-identified patent and that said Letters Patent is hereby corrected as shown below:

Title Page, Item (73) Assignee should read:
Board of Regents, The University of
Texas System, Austin, TX (US)

Signed and Sealed this

Twenty-second Day of December, 2009

David J. Kappos
*Director of the United States Patent and Trademark Office*